(12) United States Patent
Kumar

(10) Patent No.: US 10,737,265 B2
(45) Date of Patent: Aug. 11, 2020

(54) DEVICE AND METHOD FOR CONCOMITANT EJECTION AND SUCTION OF PERFUSATE

(71) Applicant: The Florida State University Research Foundation, Inc., Tallahassee, FL (US)

(72) Inventor: Sanjay S. Kumar, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 71 days.

(21) Appl. No.: 16/264,163

(22) Filed: Jan. 31, 2019

(65) Prior Publication Data

US 2019/0161718 A1    May 30, 2019

Related U.S. Application Data

(62) Division of application No. 15/154,256, filed on May 13, 2016, now Pat. No. 10,273,442.

(60) Provisional application No. 62/211,488, filed on Aug. 28, 2015.

(51) Int. Cl.
| | |
|---|---|
| *B01L 3/00* | (2006.01) |
| *C12M 3/00* | (2006.01) |
| *A61B 1/015* | (2006.01) |
| *C12M 3/06* | (2006.01) |
| *C12M 1/00* | (2006.01) |

(52) U.S. Cl.
CPC .......... *B01L 3/50273* (2013.01); *A61B 1/015* (2013.01); *C12M 21/08* (2013.01); *C12M 23/16* (2013.01); *C12M 23/40* (2013.01); *C12M 29/10* (2013.01)

(58) Field of Classification Search
CPC ... B01L 3/50273; C12M 21/08; C12M 23/16; C12M 23/40; C12M 29/10; A61B 1/015
See application file for complete search history.

(56) References Cited

U.S. PATENT DOCUMENTS

2008/0091061 A1 * 4/2008 Kumar .............. A61B 1/00071
600/104

* cited by examiner

*Primary Examiner* — Amber R Stiles
(74) *Attorney, Agent, or Firm* — Meunier Carlin & Curfman LLC

(57) ABSTRACT

A device and methodology for concomitant ejection and suction of a perfusate (CESOP) within a region of interest without spillover of the perfusate to a juxtaposed anatomical region. An inflow line, connected to a perfusate cistern, is coupled to an outflow line, connected to outflow control mechanisms, via an elongate rigid support. Perfusate can flow through the inflow line to the region of interest, and nearly simultaneously, the outflow line can suction the perfusate out of the region of interest. The amount of time that the perfusate remains in the region of interest is sufficient to take effect in the region of interest. The rigid support helps control the inflow and outflow lines. A micromanipulator can also be used to control the lines and application tip thereof. Either or both lines may also have adjustable flow rates therethrough and may include stoppers/regulators.

15 Claims, 31 Drawing Sheets
(22 of 31 Drawing Sheet(s) Filed in Color)

|  | Control | Epileptic |
|---|---|---|
| LII | n = 16 | n = 18 |
| sEPSC (aCSF) | | |
|   Frequency, Hz | 6 ± 1 | 7.3 ± 0.8 |
|   Amplitude, pA | 20 ± 2 | 22 ± 2 |
| sEPSC (glutamate) | | |
|   Frequency, Hz | 7.9 ± 1.6 | 6.2 ± 0.6 |
|   Amplitude, pA | 20 ± 2 | 22 ± 2 |
| sEPSC (NBQX) | | |
|   Frequency, Hz | 5.6 ± 1 | 4.9 ± 0.8 |
|   Amplitude, pA | 18 ± 1 | 21 ± 2 |
| LIII | n = 17 | n = 18 |
| sEPSC (aCSF) | | |
|   Frequency, Hz | 6.4 ± 0.7 | 8.9 ± 1* |
|   Amplitude, pA | 17 ± 1 | 24 ± 2* |
| sEPSC (glutamate) | | |
|   Frequency, Hz | 5.9 ± 0.5 | 10 ± 1*** |
|   Amplitude, pA | 16 ± 0.8 | 22 ± 2** |
| sEPSC (NBQX) | | |
|   Frequency, Hz | 4.6 ± 0.6 | 10.5 ± 1*** |
|   Amplitude, pA | 15 ± 1 | 24 ± 2*** |
| LII | n = 16 | n = 18 |
| sIPSC (aCSF) | | |
|   Frequency, Hz | 12.3 ± 1.4 | 7.9 ± 0.7** |
|   Amplitude, pA | 48 ± 7 | 52 ± 8 |
| sIPSC (glutamate) | | |
|   Frequency, Hz | 14.8 ± 2.3 | 8.5 ± 0.9** |
|   Amplitude, pA | 47 ± 6 | 44 ± 6 |
| sIPSC (NBQX) | | |
|   Frequency, Hz | 11.1 ± 1.4 | 7.5 ± 1.0* |
|   Amplitude, pA | 37 ± 3 | 42 ± 4 |
| LIII | n = 17 | n = 18 |
| sIPSC (aCSF) | | |
|   Frequency, Hz | 6.8 ± 0.7 | 7.8 ± 1 |
|   Amplitude, pA | 45 ± 4 | 47 ± 8 |
| sIPSC (glutamate) | | |
|   Frequency, Hz | 5.8 ± 0.5 | 7.6 ± 0.8 |
|   Amplitude, pA | 41 ± 3 | 40 ± 6 |
| sIPSC (NBQX) | | |
|   Frequency, Hz | 4.5 ± 0.3 | 6.8 ± 0.9 |
|   Amplitude, pA | 29 ± 2.6 | 30 ± 2 |

*FIG. 8*

DEVICE AND METHOD FOR CONCOMITANT EJECTION AND SUCTION OF PERFUSATE

CROSS-REFERENCE TO RELATED APPLICATIONS

This nonprovisional application is a divisional of and claims priority to U.S. patent application Ser. No. 15/154,256, entitled "Device and Method for Concomitant Ejection and Suction of Perfusate." filed May 13, 2016 by the same inventor, which is a continuation of and claims priority to U.S. Provisional Patent Application Ser. No. 62/211,488, entitled "Method for Concomitant Ejection and Suction of Perfusate Using Microfluidic Device", filed Aug. 28, 2015 by the same inventor, the entireties of which are incorporated herein by reference.

BACKGROUND OF THE INVENTION

1. Field of the Invention

This invention relates, generally, to microfluidic devices. More specifically, it relates to microfluidic devices for ejection and suction of drugs/compounds.

2. Brief Description of the Prior Art

Perfusion involves a procedure of delivering a drug or nutrients to an internal organ or tissue via the bloodstream. The most popular methods of accomplishing this are bath perfusions and local perfusions, which have both proven cumbersome and/or inadequate for studying how drug application to one region of the brain affects a neighboring/juxtaposed region.

During a perfusion, it is common for flow conditions to be turbulent or non-laminar. Manifested in slice recording chambers, these conditions exacerbate spillover, thereby hindering/disrupting electrophysiological recordings and the study of region-specific drug effects.

Accordingly, what is needed is an improved microfluidic device and methodology that effectuates perfusion in these turbulent/non-laminar flow conditions. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for improved perfusion in turbulent/non-laminar flow conditions is now met by a new, useful, and nonobvious invention.

In an embodiment, the current invention is a device for concomitant ejection and suction of a perfusate within a region of interest (ROI) without spillover of the perfusate into a juxtaposed anatomical region. The device includes an inflow manifold and an outflow manifold, where the proximal end of the inflow manifold is connected to a cistern (e.g., multi-barrel perfusion system coupling multiple reservoirs) containing the perfusate and the proximal end of the outflow manifold is connected to a reservoir and an outflow control mechanism that controls suction rate of the perfusate out of the ROI and into the reservoir. The inflow and outflow manifolds are directly or indirectly coupled to each other (e.g., a rigid support member such as an elongate rod disposed between the manifolds).

An inflow tip is disposed at the distal end of the inflow manifold, and similarly, an outflow tip is disposed at the distal end of the outflow manifold. The inflow and outflow tips collectively form the device's application tip. This application tip both discharges and suctions perfusate into and out of the ROI nearly simultaneously while allowing the perfusate to effectuate a reaction within the ROI or the juxtaposed region. Specifically, the outflow manifold nearly simultaneously suctions perfusate out of the ROI as the inflow manifold discharges it. This is done so that the perfusate cannot spillover into the juxtaposed region from the ROI.

The inflow manifold may further be coupled to an inflow control mechanism (e.g., stopper or regulator). Similarly, the outflow control mechanism may include a stopper or regulator as well, or may be a variable speed peristaltic pump. Alternatively, the inflow manifold may operate under gravity-fed negative pressure.

The inner diameter of the outflow tip (e.g, 750 µm) may be larger than the inner diameter of the flow tip (e.g., 250 µm). Further, the inflow and outflow tips may be staggered at their distal tips. Additionally, the flow rate of perfusate through the outflow manifold may be faster than the flow rate of perfusate through the inflow manifold. Each of these features helps ensure that all perfusate that is discharged by the inflow manifold is immediately suctioned out by the outflow manifold.

To further control the application tip, the device may also include a micromanipulator to position the application tip precisely within the ROI.

In a separate embodiment, the current invention is a method of concomitant ejection and suction of a perfusate within an ROI without spillover of the perfusate into a juxtaposed anatomical region. An apparatus is provided, comprising an inflow manifold, an outflow manifold, and an application tip formed of an inflow tip of the inflow manifold and an outflow tip of the outflow manifold disposed adjacent to each other. The inflow and outflow manifolds are coupled to each other via an elongate rigid support member to permit precise positioning of the application tip. The proximal end of the inflow manifold is coupled to a cistern containing the perfusate to be delivered to the ROI. The proximal end of the outflow manifold is coupled to a reservoir and an outflow control mechanism to control a rate of suction of the perfusate out of the ROI and into the reservoir.

The application tip is positioned within the ROI, the perfusate is discharged into the ROI through the inflow manifold, and the perfusate is simultaneously suctioned out of the ROI through the outflow manifold. This application tip both discharges and suctions perfusate into and out of the ROI nearly simultaneously while allowing the perfusate to effectuate a reaction within the ROI or the juxtaposed region. Specifically, the outflow manifold nearly simultaneously suctions perfusate out of the ROI as the inflow manifold discharges it. This is done so that the perfusate cannot spillover into the juxtaposed region from the ROI.

The flow rate of the perfusate through the inflow manifold can be adjusted to be lower than the flow rate of the perfusate through the outflow manifold. Further, the flow rate of the perfusate through the outflow manifold can be adjusted as well.

In other embodiments, the current invention can include any one or more of the foregoing features.

It is an object of the current invention to provide rapid and focal delivery of drugs/compounds to regions of interest within the tissue with minimal or no spillover, with fine control of the application area. It is a further object of the current invention to provide mobility within the restricted environs of the recording chamber/scope. Its "electrode-like" configuration enables movement of the device's application tip freely on the tissue surface to scout for "hot-spots" within the tissue that evoke responses in the recorded neurons. It is yet another object of the current invention to provide savings in previous drug volumes while assaying drug effects, to provide feasibility for assaying reversibility of drug effects, and to provide a cost-effective solution for manufacture.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 3A depicts in the lower illustration a plot of the paired-pulse ratio as a function of inter-stimulus interval for LII stellate cells from control and epileptic rats.

FIG. 3B depicts in the lower illustration a plot of the normalized EPSC amplitude as a function of stimulus number.

FIGS. 3A-3F show that LII stellate cells, but not LIII pyramidal neurons, in MEA have enhanced paired-pulse facilitation under epileptic conditions.

FIG. 4C depicts in the lower illustration differential effects of focal application of TTX (1 µM) in PrS on action potential discharge of a RS cell in LIII of PrS, triggered by depolarizing current injections.

FIGS. 5E-5H show that synaptic inhibition is significantly reduced in epileptic rats as is inhibitory synaptic drive from PrS.

FIGS. 6A-6D show that excitatory synaptic drive is significantly enhanced in epileptic rats despite PrS influence being masked.

FIGS. 6E-6H show that synaptic inhibition is not compromised in epileptic rats.

FIG. 8 is a table summarizing frequency and amplitude of postsynaptic currents in MEA neurons from control and epileptic groups. Values represent means±SE. The total number of cells tested (n) is indicated for each group under the indicated conditions. aCSF, glutamate and NBQX were applied locally in PrS. Frequency is reported in Hz, and amplitude in pA. sEPSCs, spontaneous excitatory postsynaptic currents; sIPSCs, spontaneous inhibitory postsynaptic current; PrS, presubiculum; MEA, medial entorhinal area. *$P<0.05$, $P<0.01$, *$P<0.001$, t-test.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In an embodiment, the current invention is a microfluidic device that enables focal application and clearance of drugs/compounds (perfusate) to and from nuclei or target regions, such as within acute brain slices submerged in artificial cerebrospinal fluid (aCSF) or other bathing media under non-laminar/turbulent flow conditions. The technique of concomitant ejection and suction of perfusate (CESOP) has distinct advantages over bath perfusion and local perfusion, both of which have proven cumbersome and/or inadequate for studying how drug application to one region of the brain affects a neighboring/juxtaposed region.

The CESOP device/method enables rapid focal application of drugs/compounds, while restricting their "spillover" to neighboring regions. Turbulent/Non-laminar flow conditions that manifest in slice recording chambers exacerbate spillover, thereby hindering/disrupting electrophysiological recordings and the study of region-specific drug effects. The CESOP device/method solves this problem through concomitant ejection and suction of perfusate, even under moderately turbulent conditions.

In an embodiment, CESOP is a gravity-led device/method comprising a uniquely fabricated microfluidic tip (e.g., formed of polypropylene) with a pair of tapered manifolds (of differing diameters) that piggy-back on each other to form a fine "application tip". The smaller-diameter manifold is connected to the perfusate cistern and is under gravity-fed positive pressure, while the larger-diameter manifold constitutes a suction/outflow line and is under gravity-fed negative pressure, which when "primed" and guided below the recording chamber, generates a partial vacuum for concomitant suction of the perfusate.

The application tip, along with tubing, are rendered mechanically stable by fastening them to a solid (metal) rod that can then be mounted onto a mechanical or motorized manipulator for maneuverability within the recording chamber. The drug application area within the region of interest (ROI) can thus be controlled by regulating the outflow line.

EXAMPLE

Figure 1:
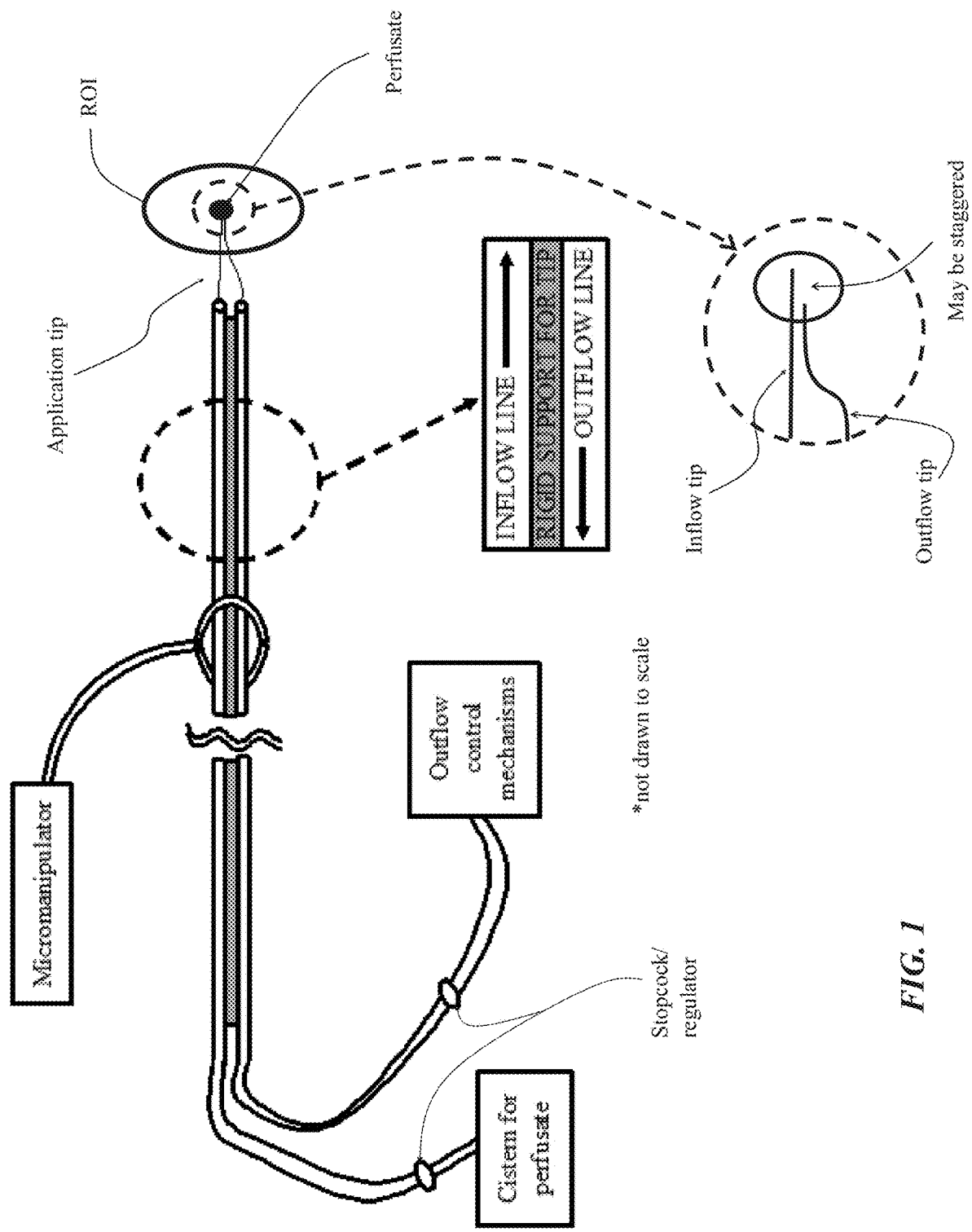
FIG. 1 is a schematic depicting a CESOP device, according to an embodiment of the current invention.

FIG. 1 is a schematic of a microfluidic CESOP device according to a structural embodiment of the current invention, alternatively, FIG. 1 shows an exemplary structure that may be used in an embodiment of the current methodology. The device includes an inflow line/tubing/manifold having a proximal end and a distal end, where the proximal end is coupled to a conventional cistern in a conventional manner (i.e., using standard connectors, etc.). The cistern contains the perfusate to be delivered to the ROI. Various control mechanisms may also be disposed on and coupled to the proximal end of the inflow line, where the control mechanisms control the rate of inflow of the perfusate from the cistern to the ROI.

The device further includes an outflow line/tubing/manifold having a proximal end and a distal end, where the proximal end is coupled to conventional mechanisms to control the rate of outflow/suction of the perfusate from the ROI.

Alternatively, the inflow line may operate under gravity positive pressure, and the outflow line may operate under gravity-fed negative pressure, as previously discussed.

The inflow line and/or the outflow line can include a stopcock/regulator to further control the flow of perfusate through the respective manifolds.

Typically, the outflow line has a larger internal diameter than the inflow line, due in part to the inflow line typically needing a precise (though many times adjustable) rate of inflow of perfusate, and the outflow line typically having a constant rate of outflow/suction. Also, the outflow line is ensured to suction anything discharged from the inflow line, regardless of rate of flow through the inflow line.

The distal end of the inflow line includes an inflow tip, and the distal end of the outflow line includes an outflow tip. The inflow tip and the outflow tip are disposed in very close proximity to each other (essentially adjacent to each other) and collectively form the application tip, as seen in FIG. 1. The inflow tip and outflow tip may even be coupled or otherwise secured together. In this way, as the perfusate is discharged from the inflow line in the ROI, the outflow line can nearly immediately suction the perfusate out of the ROI. The time that the perfusate makes contact with the ROI would be sufficient to notate any change or effect of the perfusate. That change or effect can be within that ROI itself or within a juxtaposed ROI. Suction of the outflow line prevents spillover or leaking from the first ROI into the juxtaposed ROI.

The inflow line and the outflow line may be indirectly coupled together via a rigid support member, such as a solid metal rod. The rigidity of the support member permits an operator thereof to move the support member (manually or automatically) and thus move the inflow line and outflow line together. As such, wherever the inflow line discharges the perfusate in the ROI, the outflow line is always present to nearly instantaneously suction the perfusate out of the ROI. The rigid support member also permits precise positioning of the application tip.

As briefly noted previously, in use, the CESOP device (typically the rigid support member) may be coupled to or otherwise controlled by a micromanipulator or other mechanical or motorized manipulator that moves and permits precise positioning of the application tip within the ROI.

Testing

An embodiment of the current invention was fabricated and tested in Saad Abassi and Sanjay S. Kumar, Layer-specific modulation of entorhinal cortical excitability by presubiculum in a rat model of temporal lobe epilepsy, *J Neurophysiol*, 114: 2854-2866, 2015, which is incorporated herein by reference in its entirety. Though this study had an objective of assessing how the presubiculum (PrS) affects excitability of the medial entorhinal area (MEA) in a rat model, as it relates to temporal lobe epilepsy (TLE), this study also enables use of the CESOP technique/device as it would be applied in a real-world setting, thus showing effectiveness of CESOP.

Preliminarily, the PrS and the MEA were confirmed to have strong connectivity when PrS afferents were electrically stimulated while neurons from the superficial layers of the MEA were recorded. It is known that PrS provides an anatomically robust and functionally significant input to the MEA that is both glutamatergic and GABAergic in nature. As it relates to temporal lobe epilepsy, PrS stimulation can drive hyperexcitability of superficial MEA neurons, and changes in functional network connectivity with the MEA enables the PrS to promote epileptiform activity in the superficial layers. Conversely, chemical ablation of the PrS input to the MEA provides partial protection against epilepsy-related cell loss in a particular region of the MEA.

It is important to note that within a brain slice of the rat model, the PrS and the entorhinal cortex are juxtaposed or otherwise in close proximity to one another, separated only by the parasubiculum. This aspect is important because certain embodiments of the current invention are particularly beneficial when the regions of interest are in close proximity to each other. For example, devices exist that permit local perfusion if the two regions of interest are sufficiently spatially far enough from each other to avoid spillover between regions. Further, devices also exist if spillover between juxtaposed regions of interest is of no concern. However, no device exists that permits local perfusion if the two regions of interest are juxtaposed or are otherwise in close proximity to each other, where spillover is likely and also detrimental.

Herein, the role of PrS input on the excitability of LII and LIII neurons in the MEA was examined, as well as PrS-mediated alterations in their synaptic drive under chronically epileptic conditions. Thus, it was important that pharmaceutical agents could be focally delivered to the PrS without any spillover to the MEA. Spillover of the pharmaceutical agents to the MEA would compromise the results sought herein and would ultimately be detrimental to the current study.

I. Materials and Methods

A. Animals

Sprague-Dawley rats (male; n=11 epileptic, n=15 controls) from postnatal (P) days 40 to 88 were used in this study. All experiments were carried out in accordance with the National Institute of Health Guide for the Care and Use of Laboratory Animals and were approved by the Florida State University Institutional Animal Care and Use Committee. Rats were made epileptic according to previously described protocols for bringing up the pilocarpine model of TLE. Briefly, rats were treated with pilocarpine (P41, 141±2 g; 380 mg/kg i.p.) 20 min after atropine methylbromide (5 mg/kg i.p.). Diazepam (10 mg/kg i.p.) was administered 2 h after the onset of status epilepticus and repeated as needed. Following recovery from status epilepticus, rats were video monitored (40 h/wk) for spontaneous seizures. Animals used for electrophysiological experiments were confirmed epileptic, displaying frank spontaneous recurrent seizures scored 3 or greater on the Racine scale (Racine 1972) on two or more observations during the 40 h/wk video monitoring. Recordings from epileptic animals were made on average 39 days (P80) post status epilepticus (range: 25-47 days, P66-P88), with initial seizures observed between 5 and 29 days post status. Control groups consisted of naïve rats that were on average P70 (range: P49-P91).

B. Slice Preparation and Electrophysiology

Figure 2A:
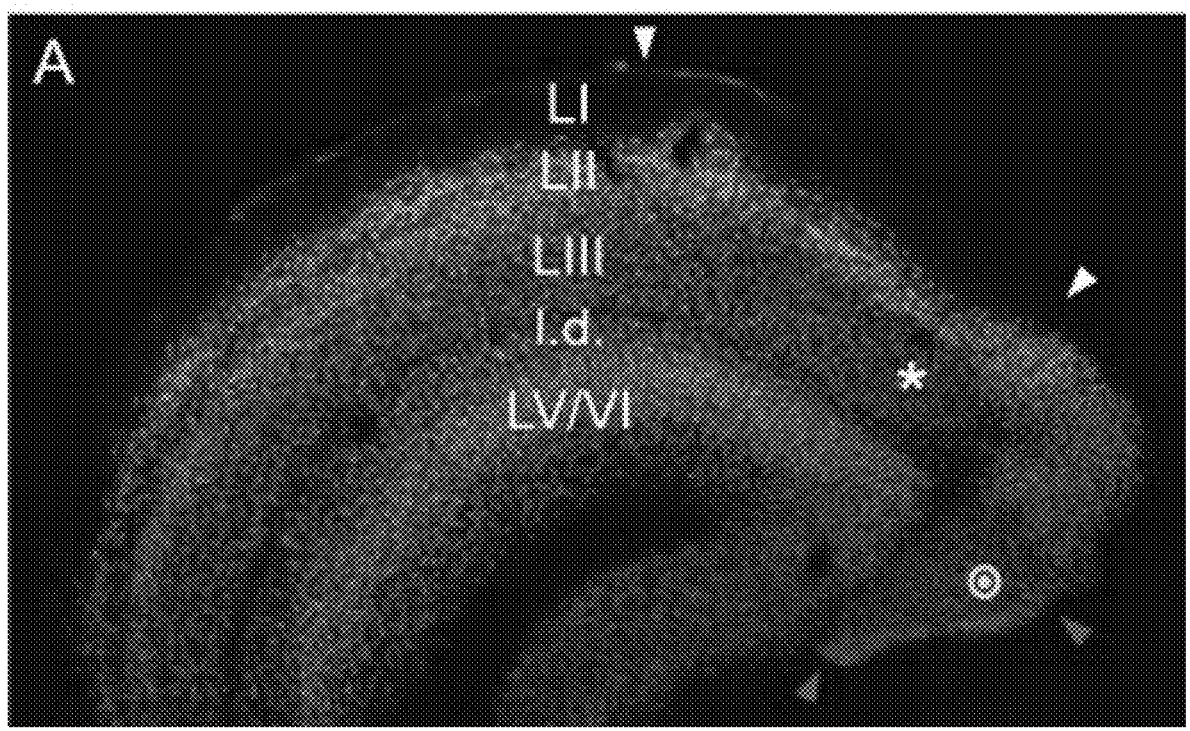
FIG. 2A depicts an acute brain slice from a control rat. Note that no loss of LIII neurons in MEA (*) can be seen. Arrows indicate boundaries of MEA (white) and PrS (red) along the pial surface. General location of stimulating electrode placement in PrS is indicated by the bulls-eye.
Figure 2B:
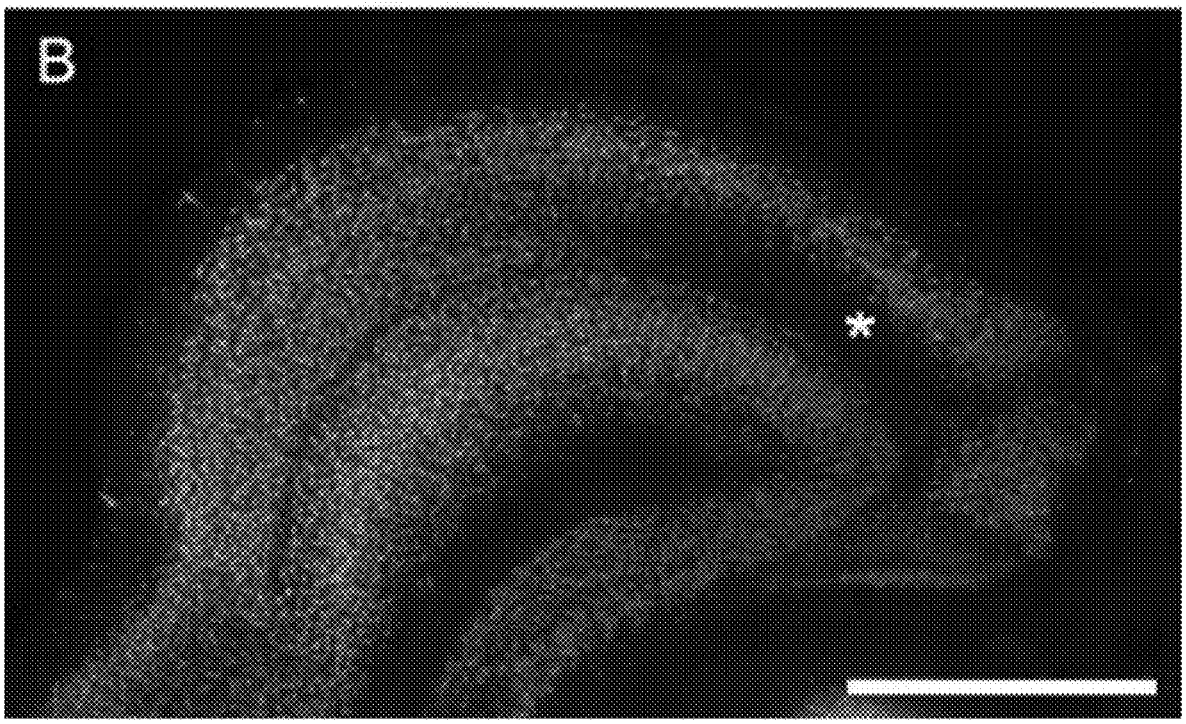
FIG. 2B depicts an acute brain slice an epileptic rat, where, NeuN-labeled sections show characteristic loss of LIII neurons in MEA (*). The scale bar indicates 1 mm.
Figure 2C:
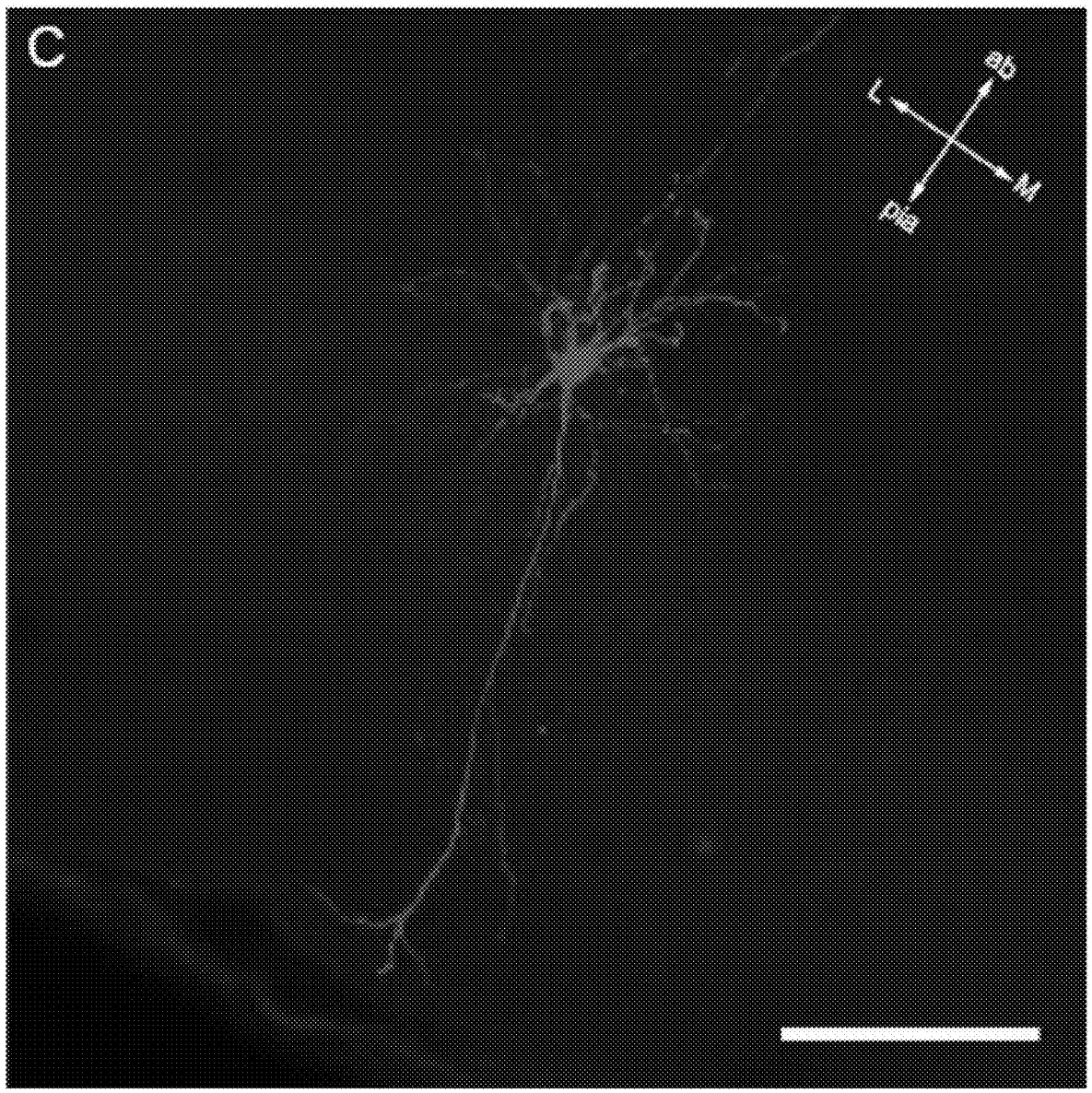
FIG. 2C depicts gross morphology of a biocytin-labeled pyramidal cell in LIII used in electrophysiological recordings (L, lateral; M, medial; ab, angular bundle; l.d. lamina dissecans). The cell shown in FIG. 2C is from control tissue. The scale bar indicates 200 µm.
Figure 2D:
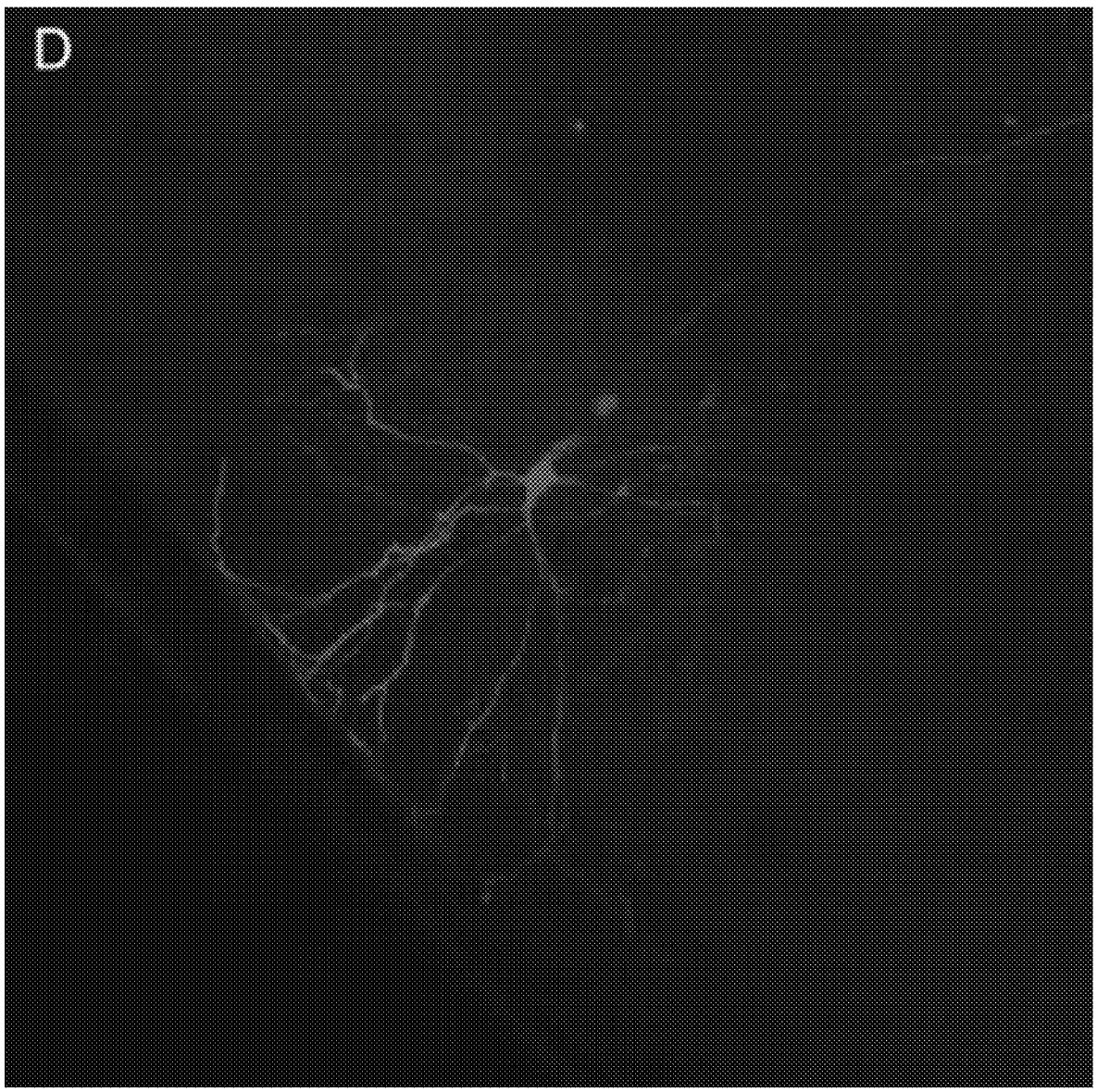
FIG. 2D depicts gross morphology of a stellate cell in LII used in electrophysiological recordings (L, lateral; M, medial; ab, angular bundle; l.d. lamina dissecans). The cell shown in FIG. 2D is from epileptic tissue.
Figure 2E:
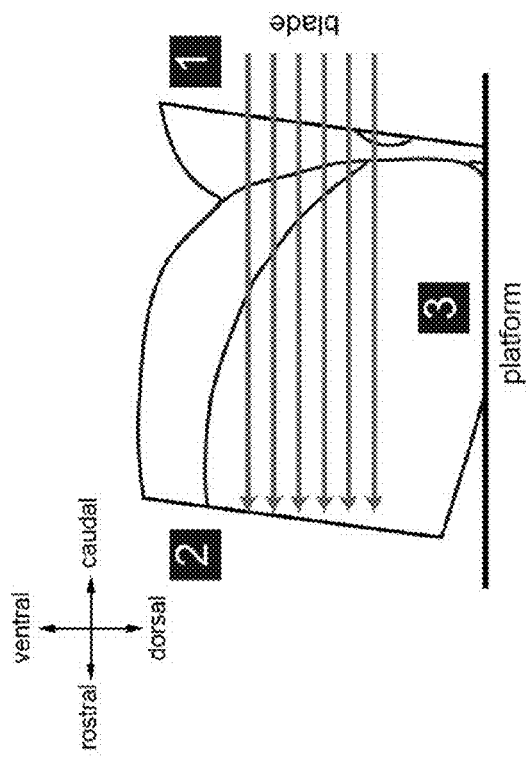
FIG. 2E depicts preparation of semi-horizontal entorhinal cortical slices retaining PrS connectivity. Initial cuts (1-3, solid red lines, left panel) are made with a razor blade. The cut surface of the brain (3, dorsal) is then glued to the vibratome platform as indicated. Horizontal arrows (right panel) indicate cutting direction. Roman numerals (I-III) indicate lamina and Scale bars: 1 mm (A, B); 200 µm (C, D).
Figure 2E:
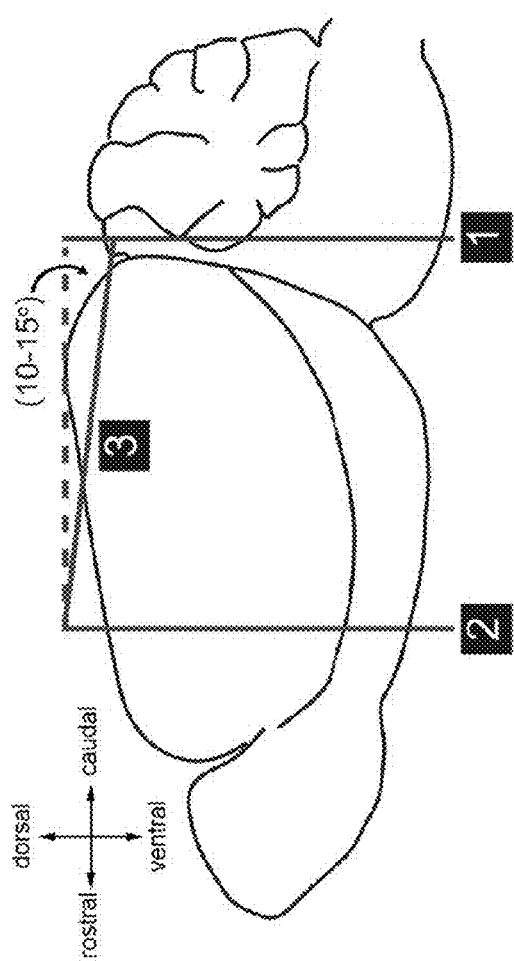

Rats were deeply anesthetized with urethane (1.5 g/kg ip) before being decapitated. Following decapitation, the brain was quickly removed from the skull before being placed in a chilled (4° C.) low-$Ca^{2+}$, low-$Na^+$ "cutting solution" containing (in mM) 230 sucrose, 10 D-glucose, 26 $NaHCO_3$, 2.5 KCl, 1.25 $NaH_2PO_4$, 10 $MgSO_4$, and 0.5 $CaCl_2$ equilibrated with a 95%-5% mixture of $O_2$ and $CO_2$. After removing the cerebellum and rostral half of the brain, a 10-15° semi-horizontal cut (in a ventral-caudal to dorsal-rostral plane) was made to the dorsal part of the cortex with respect to the horizontal plane (FIG. 2E). The cut dorsal surface of the brain was adhered to the cutting platform using cyanoacrylate glue. This cutting angle was chosen to increase the likelihood of preserving PrS projections to MEA in acute brain slices, because PrS projections tend to travel to the MEA in a lateroventral orientation. Semi-horizontal slices (400 μm) were prepared using a microslicer (VTI000S, Leica. Germany) in the chilled cutting solution and allowed to equilibrate in oxygenated artificial cerebrospinal fluid (aCSF) containing (in mM) 126 NaCl, 26 $NaHCO_3$, 3 KCl, 1.25 $NaH_2PO_4$, 2 $MgSO_4$, 2 $CaCl_2$, 0.25 L-Glutamine, and 10 D-glucose (pH 7.4), first at 32° C. for 1 h and subsequently at room temperature before being transferred to the recording chamber.

Recordings were obtained at 32±1° C. from neurons in LII and LIII of MEA under Nomarski optics (Zeiss) using a visualized infrared setup (Hamamatsu) that enabled identification of their location within the various lamina. On average, 3.5±0.4 (range: 2-5) and 3.6±0.4 (range: 2-6) cells were recorded per animals in the control and epileptic groups respectively. Patch electrodes were pulled from borosilicate glass (1.5 mm outer diameter, 0.75 mm inner diameter, 3-6 MΩ). The internal solution for voltage-clamp experiments contained (in mM): 120 cesium gluconate, 1 $MgCl_2$, 1 $CaCl_2$, 11 CsCl, 10 HEPES, 2 NaATP, 0.3 NaGTP, 1 QX-314, 11 EGTA, and 20 biocytin (pH 7.3, corrected with Cs—OH; final osmotic concentration, 290 mOsm). The internal solution for current-clamp experiments contained (in mM): 105 potassium gluconate, 30 KCl, 10 HEPES, 10 phosphocreatine, 4 MgATP, 0.3 GTP (pH adjusted to 7.3 with KOH; final osmotic concentration, 300 mOsm).

Recording conditions were the same for control and epileptic animals. Slices were maintained in oxygenated (95% $0_2$-5% $CO_2$) aCSF, flowing at a rate of 2 ml/min. Drugs were applied focally to superficial PrS via the CESOP technique (FIGS. 4A-4E, described below). Postsynaptic currents and potentials were recorded using a MultiClamp 700B amplifier and pCLAMP software (Molecular Devices, Union City, Calif.), filtered at 1-2 kHz (10 kHz for current clamp), digitized at 10-20 kHz, and stored electronically. Evoked (e) and spontaneous (s) excitatory postsynaptic currents (EPSCs) were obtained by holding the cell at −70 mV, while inhibitory postsynaptic currents (IPSCs) were recorded at a holding potential of 0 mV, close to the reversal potential for glutamate. Series resistance was monitored continuously, and those cells in which this parameter exceeded 20 MS or changed by >20% were rejected. Series resistance compensation was not used. Sodium glutamate (100 μM), 2,3-dioxo-6-nitro-1,2,3,4-tetrahydrobenzo[f]quinoxaline-7-sulfonamide (NBQX, 10 μM), Amaranth (0.4 mM), and Tetrodotoxin (TTX, 1 μM), purchased from Sigma (Sigma, St. Louis, Mo.), were prepared in aCSF, and were used in experiments accordingly.

C. Electrical Stimulation

Bipolar electrodes (CE-2C75; Fredrick Haer, Brunswick, Me.) with 25-μm tip diameters were positioned in LII or LIII of PrS slightly distal to the midpoint along a proximodistal axis spanning the subiculum to parasubiculum (FIG. 2A). Threshold (T) was defined as the minimal current required to evoke an EPSC on 50% of the trials in the recorded neuron. Stimulus intensity was set to 1.5×T, ranging between 0.2-0.8 mA, for a 50 μs stimulus pulse. Paired pulses were delivered to PrS at various inter-stimulus intervals (ISI range: 10-500 ms) at 0.2 Hz. Repeated stimulation entailed delivery of trains of stimuli (5 pulses) to the PrS at 10, 20 and 100 Hz every 5 s.

D. Focal Application of Compounds within PrS

Experimental compounds were focally applied to the PrS using CESOP to minimize spillover into neighboring nuclei, especially under turbulent or non-laminar flow conditions in the recording chamber. This system consisted of two perfusion pipettes piggy-backed onto one another and staggered such that the longer, narrower pipette (e.g., ~250 µm) served as the inflow line, while the other, with a slightly larger tip diameter (~750 µm), served as the outflow. The inflow perfusion pipette was attached to a multi-barrel gravity fed perfusion system coupling multiple drug reservoirs, and enabling rapid exchange of experimental solutions. The outflow line consisted of a single line attached to a variable speed peristaltic pump for suction of ejected perfusate. To minimize spread of chemical compounds outside the region of interest, flow rates for "in" and "out" lines were adjusted to ~0.04 ml/min and ~0.7 ml/min, respectively.

Amaranth, a food coloring dye, dissolved in aCSF was used for visual identification of the perfusate and calibration of flow rate. Following placement of the CESOP electrode in the bath (aCSF) just above the superficial PrS, flow rates in both in and out lines were adjusted to restrict perfusate to the region of interest before switching to normal aCSF. The pressure head used in these experiments (~20 ml) was sufficient to maintain a near constant flow rate throughout the recording session (<5 ml used, FIG. 4E top panel). PrS-MEA connectivity was confirmed via electrical stimulation within PrS prior to CESOP and baseline measurements of sEPSCs and sIPSCs were recorded in aCSF following complete exchange of fluid in the inflow line (~1 min). To confirm restriction of the perfusate to the region of interest, the dye laden aCSF was re-perfused at the end of each recording session.

E. NeuN-Biocylin Immunohistochemistry

Neurons were filled with biocytin during recording (20 mM, included in the internal solution). To visualize biocytin-labeled neurons after recording, slices were fixed in 4% paraformaldehyde in 0.1 M phosphate buffer (PB. pH 7.4) at 4° C. for at least 24 h. After fixation, slices were stored in 30% ethylene glycol and 25% glycerol in 50 mM PB at −20° C. before being processed with a whole-mount protocol with counterstaining by NeuN immunocytochemistry. Slices were rinsed in 0.5% Triton X-100 and 0.1 M glycine in 0.1 M PB and then placed in a blocking solution containing 0.5% Triton X-100, 2% goat serum (Vector Laboratories, Burlingame, Calif.), and 2% bovine serum albumin in 0.1 M PB for 4 h. Slices were incubated in mouse anti-NeuN serum (1:1,000; MAB377, Chemicon, Temecula, Calif.) in blocking solution overnight. After a rinsing step, slices were incubated with the fluorophores Alexa 594 streptavidin (5 µg/ml) and Alexa 488 goat anti-mouse (10 µg/ml; Molecular Probes, Eugene, Oreg.) in blocking solution overnight. Slices were rinsed, mounted on slides and coverslipped with Vectashield (Vector Laboratories) before being examined with a confocal microscope (TCS SP2 SE, Leica).

F. Data Analysis

The spontaneous postsynaptic current data, obtained from 1-min-long continuous recordings, were analyzed with Mini Analysis (Synaptosoft, Decatur, Ga.). The threshold for event detection was set at 3× root mean square noise level and software-detected events were verified visually before measuring their frequency and amplitude. A hundred consecutive events from each cell under each condition were pooled together to assay for significant shifts in cumulative probability distributions of inter-event intervals or amplitude using the nonparametric Kolmogorov-Smirnoff (K-S, IBM SPSS 20) test. Statistical significance was at p<0.05. Kinetic properties of sEPSCs and sIPSCs were obtained from rise times (RT; 10-90%) and decay time constants (τ) of single exponential fits of the averaged composite response of all events recorded within the 1 min interval.

Whole-cell current-clamp recordings were obtained in response to injection of 1) 100 pA of depolarizing current and 2) hyper- and depolarizing current steps, 600 ms in duration with amplitude ranging from −200 to 400 pA, delivered in 50 pA steps. Analysis of current-clamp experiments, and evoked EPSCs were carried out in Clampfit (Molecular Devices, Union City, Calif.). Paired pulse ratio was defined as the peak amplitude of the second evoked response relative to the peak amplitude of the first (eEPSC 2/eEPSC 1), with amplitudes measured from the baseline at start of stimulation, and determined from the averaged composite trace of a minimum of 10 individual sweeps. Amplitude measurements during repeated stimulation were measured relative (%) to the first response and determined from an average of 10 or more sweeps. Measurements are presented as mean±SEM and statistical differences ascertained with the paired and unpaired two-tailed Student's t-tests, unless otherwise indicated.

II. Results

A. Synaptic Properties of PrS Input to MK4 are Altered in Epileptic Rats

Figure 3A:
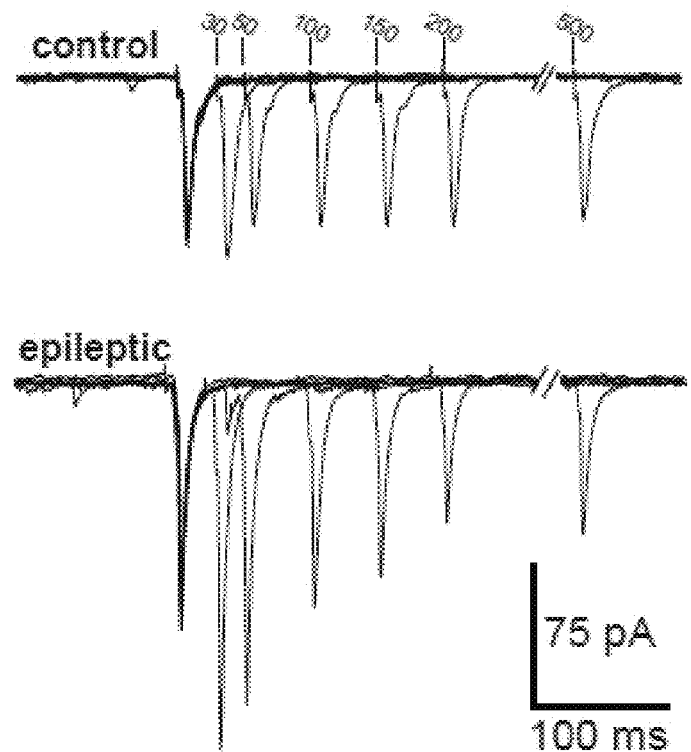
FIG. 3A depicts in the upper illustration superimposed traces of EPSCs evoked in LII stellate cells in response to paired-pulse stimulation of PrS at the indicated inter-stimulus intervals from control and epileptic rats. Each trace shown in this figure is an average of ≥5 consecutive sweeps.
Figure 3A:
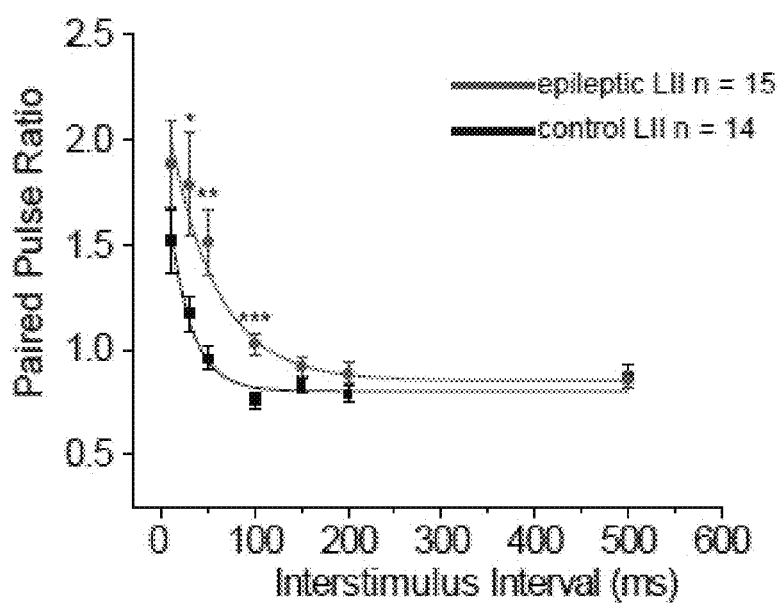
Figure 3B:
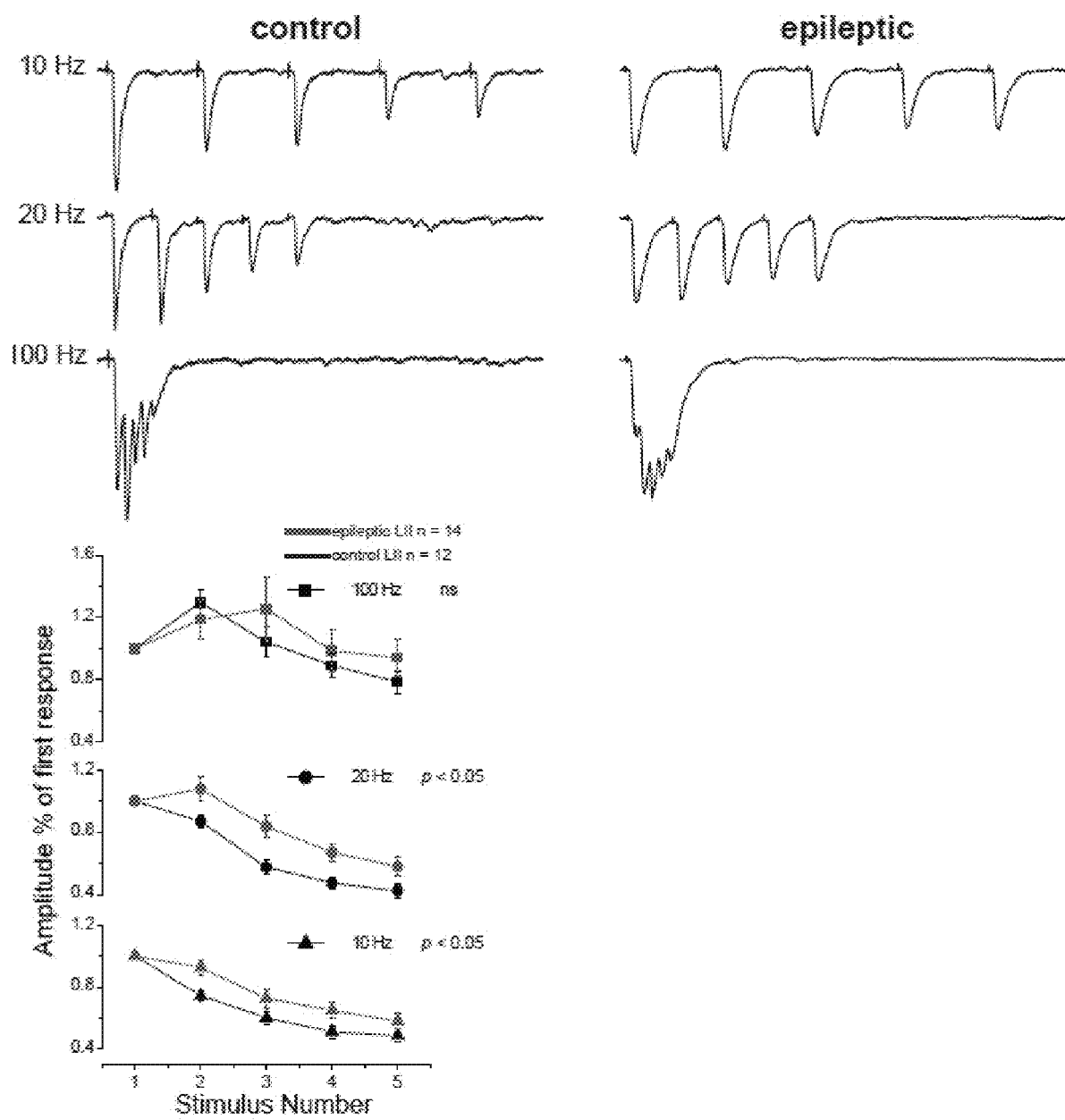
FIG. 3B depicts in the upper illustration trains of EPSCs evoked in LII stellate cells by repeated stimulation (5 pulses) of PrS at the indicated frequencies in control and epileptic rats.

Assessments of PrS contribution to MEA excitability were obtained through voltage-clamp recordings (~70 mV holding potential) from stellate cells in LII and pyramidal neurons in LIII of MEA under control and epileptic conditions (FIGS. 2A-2E). EPSCs were evoked by electrically stimulating the superficial PrS (50 µs, 0.2 Hz, 1.5×threshold) with paired stimuli delivered at various inter stimulus intervals (ISI, range: 10-500 ms; FIGS. 3A & 3D) to ascertain electrical connectivity and examine synaptic properties. In addition to paired-pulse stimulation, PrS was repeatedly stimulated (trains of 5 pulses) at frequencies ranging between 10 and 100 Hz (FIGS. 3B & 3E) to examine burst-response characteristics of MEA neurons.

In response to paired stimulation of PrS, LII stellate cells from control rats showed paired-pulse facilitation for ISIs≤50 ms, and paired-pulse depression for ISIs>50 ms (FIG. 3A). Paired-pulse facilitation in epileptic rats was significantly enhanced (p<0.05, FIG. 3A) and was maintained across a broader ISI range (≤100 ms) compared with controls. No significant differences were observed in the paired-pulse ratios beyond 100 ms between the two groups (p>0.15, t-test, FIG. 3A). In response to repeated electrical stimulation, stellate cells in epileptic rats were less depressed compared with controls between 10 and 20 Hz (p<0.05, unpaired t-test, FIG. 3B lower panel). Given that neither mean amplitudes (control: 126±21 pA; epileptic: 133±28 pA), latencies (control: 4.2±0.2 ms; epileptic: 4.8±0.2 ms) nor thresholds (control: 0.2±0.04 mA; epileptic: 0.2±0.03 mA) of individually evoked EPSCs were significantly different between control and epileptic rats (p>0.1 for all, t-test), these results suggest that neurotransmitter release properties at PrS excitatory inputs onto LII stellate cells are changed under epileptic conditions.

In response to paired stimulation of PrS, LIII pyramidal cells from control rats showed paired-pulse facilitation for ISIs≤50 ms, and paired-pulse depression for ISIs>50 ms (FIG. 3D). Unlike LII stellate cells, paired-pulse facilitation in LIII pyramidal cells was unaltered in epileptic rats (p>0.2. FIG. 3A). In response to repeated electrical stimulation, pyramidal cells showed an overall depression to successive pulses in the train at all frequencies tested (FIG. 3E), and these observations were similar between control and epileptic animals (p>0.1, t-test). Given that mean amplitudes (control: 90±13 pA, epileptic: 106±15 pA), latencies (control: 4.8±0.3 ms, epileptic 5.0±0.3 ms) and thresholds (control 0.2±0.04 mA; epileptic 0.2±0.02 mA) of individually evoked EPSCs were also similar between control and epileptic rats (p>0.3 for all, t-test), it can be inferred that PrS excitatory inputs onto LIII pyramidal cells are unaffected under epileptic conditions. Together, the evoked data suggests that excitatory inputs from PrS to LII stellate cells and LIII pyramidal neurons in MEA are functionally distinct.

Figure 3C:
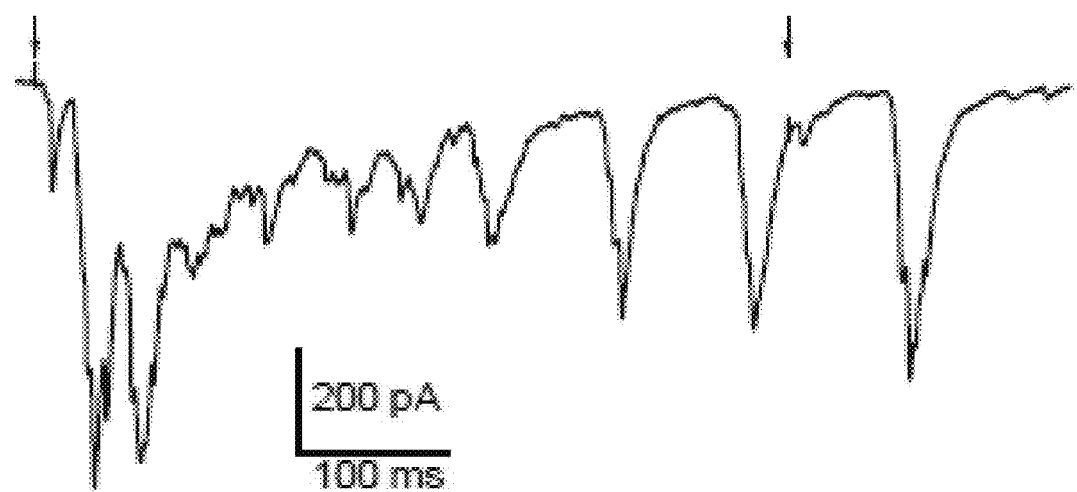
FIG. 3C depicts a typical epileptiform discharge recorded in LII stellate cell from an epileptic rat following PrS stimulation (arrows).
Figure 3D:
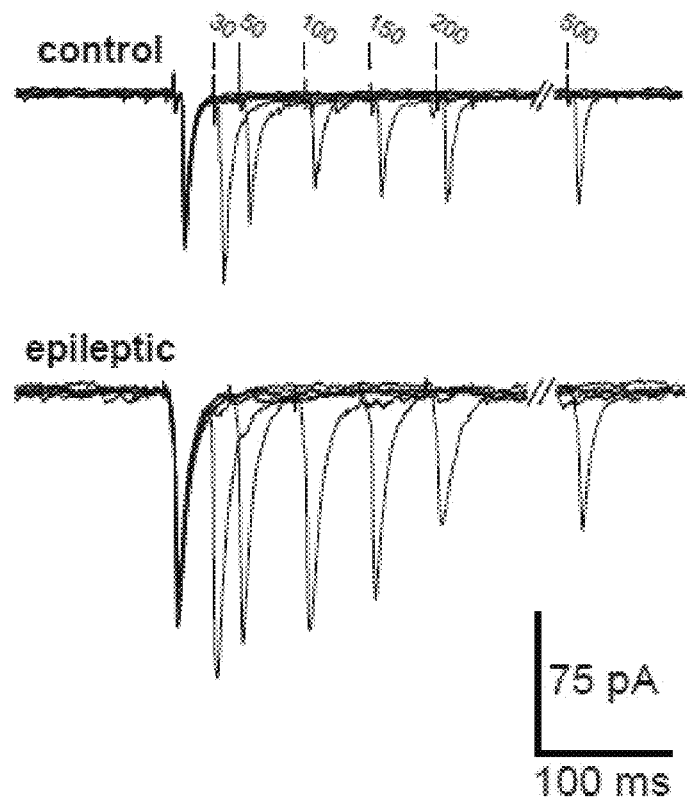
FIG. 3D depicts data from LIII pyramidal neurons corresponding to experimental manipulations described above for LII stellate cells (specifically FIG. 3A).
Figure 3D:
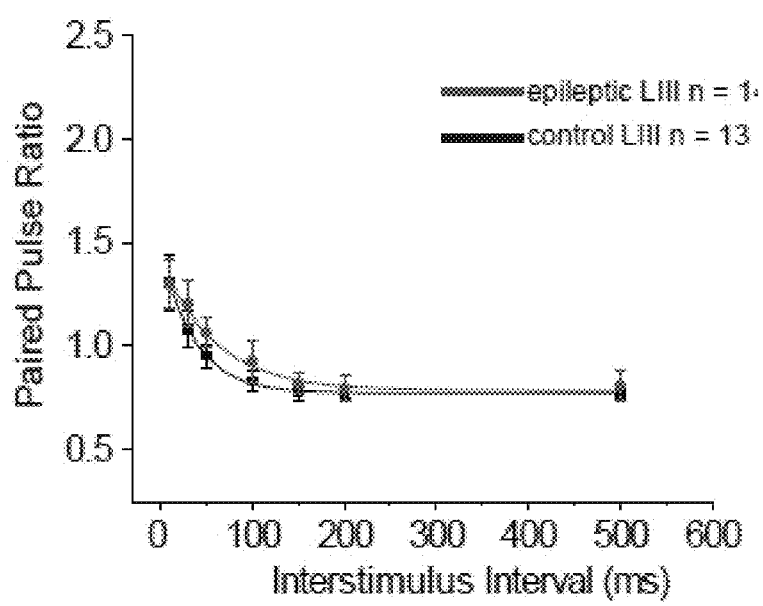
Figure 3E:
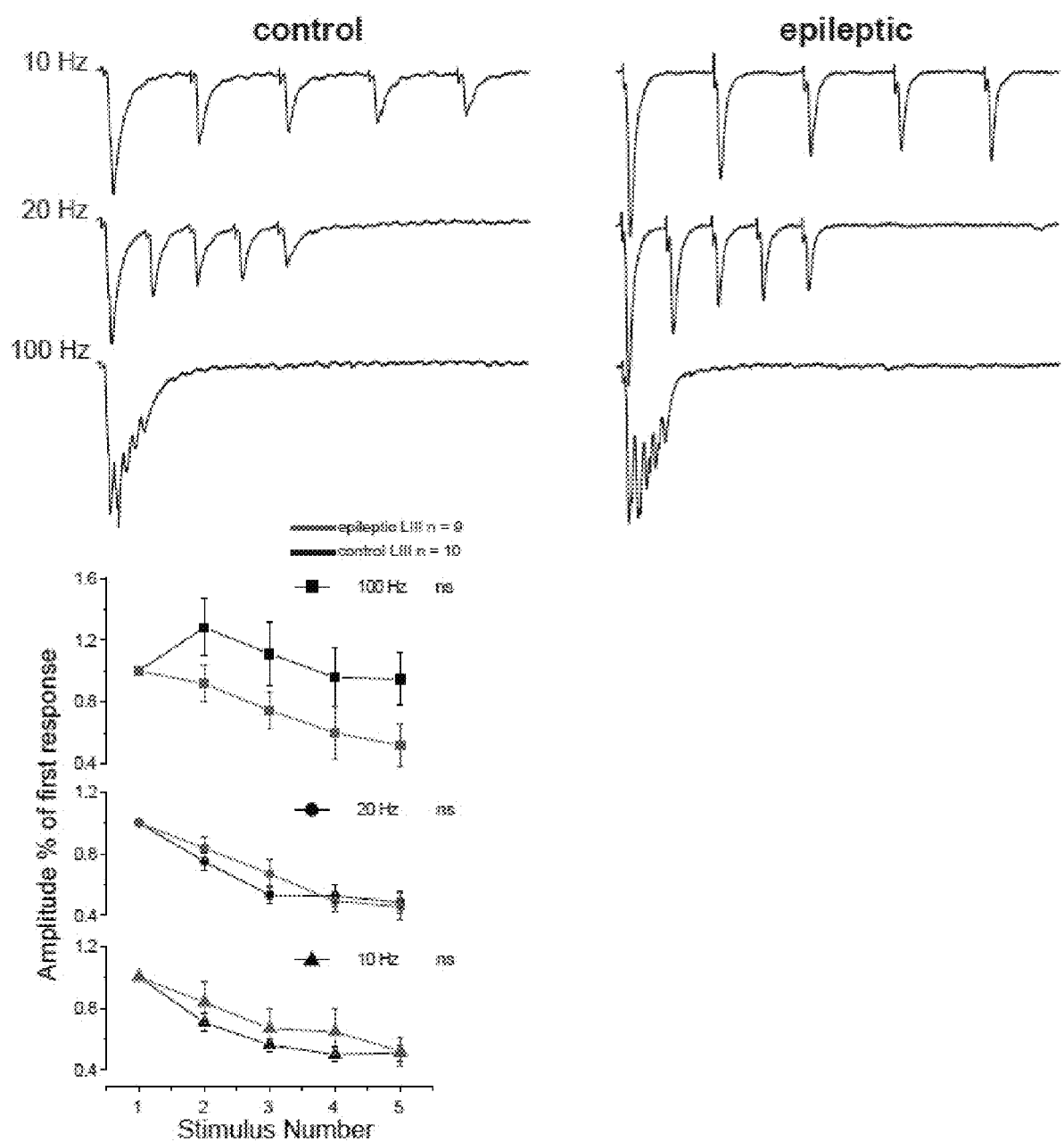
FIG. 3E depicts data from LIII pyramidal neurons corresponding to experimental manipulations described above for LII stellate cells (specifically FIG. 3B). The scale bars in the top illustration of FIGS. 3A & 3D are applicable to the top illustrations of FIGS. 3B & 3E, respectively.
Figure 3F:
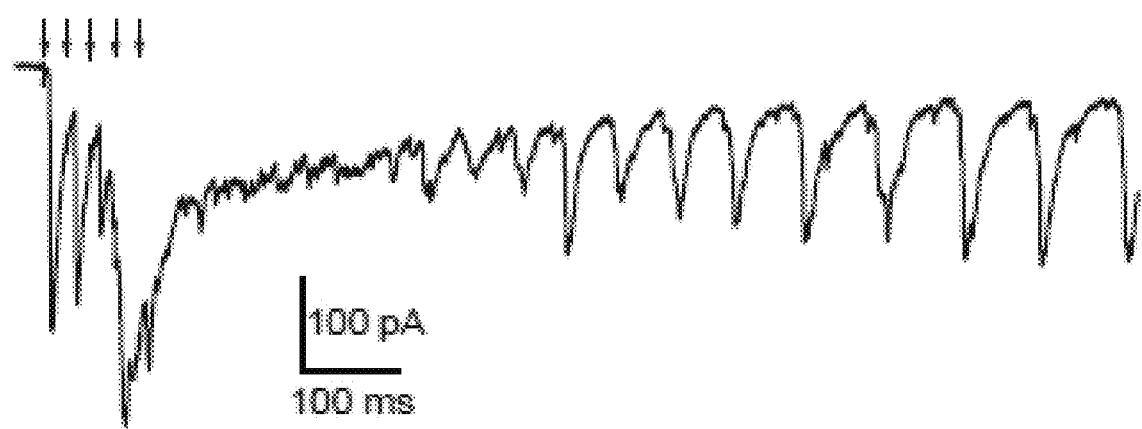
FIG. 3F depicts data from LIII pyramidal neurons corresponding to experimental manipulations described above for LII stellate cells (specifically FIG. 3C). * $p<0.05$;  $p<0.01$; * $p<0.001$, t-test. Overall.

In the process of comparing PrS-MEA connectivity through PrS stimulation in control and epileptic rats, it was observed that large amplitude population discharges triggered in both pyramidal and stellate cells in epileptic rats but not in control rats (FIGS. 3C & 3F). These observations appear consistent with TLE-related pathophysiology in the entorhinal cortex, and suggest that PrS is capable of triggering epileptiform activity in MEA neurons under chronically epileptic conditions.

B. Assessment of PrS-Mediated Synaptic Drive to MEA Neurons

The current inventors previously showed that regular-spiking (RS) neurons in the PrS are hyperexcitable in epileptic animals (Abbasi S, and Kumar SS. Regular-spiking cells in the presubiculum are hyperexcitable in a rat model of temporal lobe epilepsy. *Journal of neurophysiology* 112: 2888-2900, 2014). To assess the influence of RS neuron hyperexcitability on stellate cells in LII and pyramidal neurons in LIII of MEA and assay potential alterations in PrS-MEA connectivity, changes in excitatory and inhibitory synaptic drive to these neurons were measured following focal application of either glutamate or NBQX to the PrS in control and epileptic tissue.

Figure 4A:
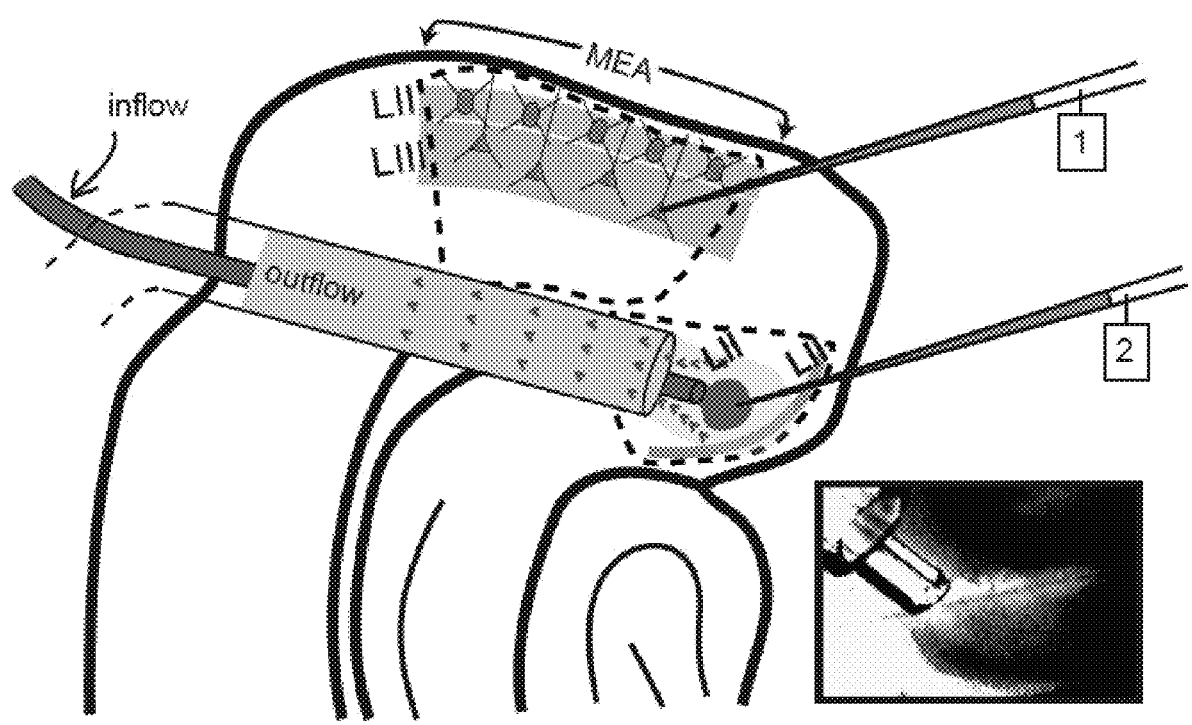
FIG. 4A is a schematic of an embodiment of the CESOP system and methodology in use. The red circle represents the perfusate applied via CESOP while recording from superficial layers of MEA (1) or locally within PrS (2). Inset: an IR-DIC image (magnification: ×10) of the CESOP electrode showing piggy-backed inflow and outflow lines.
Figure 4B:
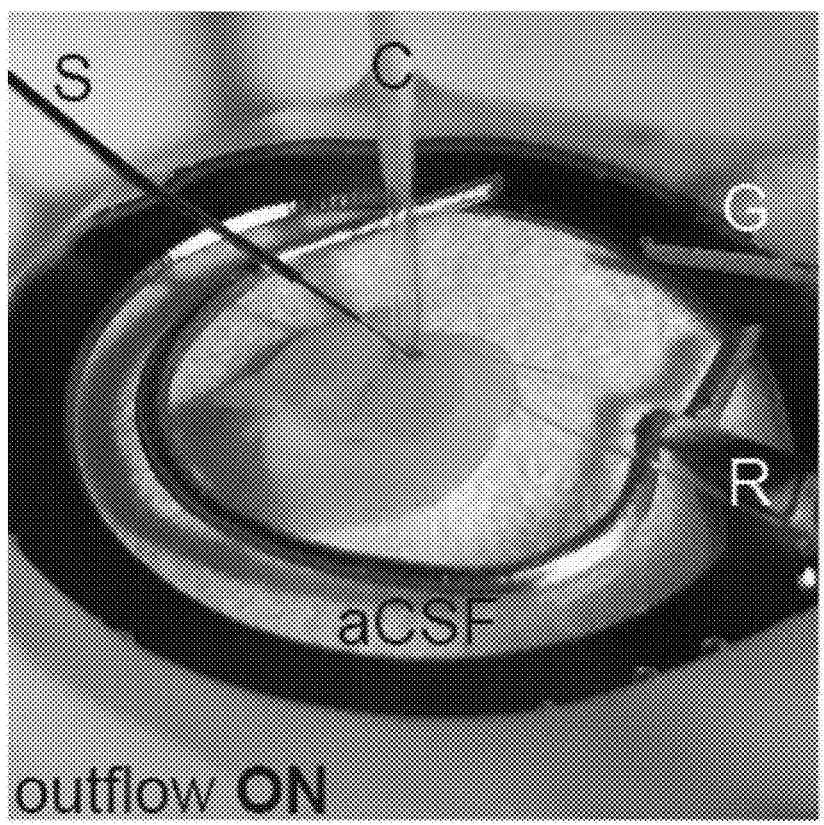
FIG. 4B are photos of the CESOP system/methodology in use. Note diffusion of dye-laden aCSF (for visualization and calibration) when the outflow line of CESOP is turned off during focal application of perfusate to the PrS in a brain slice submerged in aCSF in a recording chamber (electrodes: S, stimulating; C, CESOP; G, ground; R. recording).
Figure 4B:
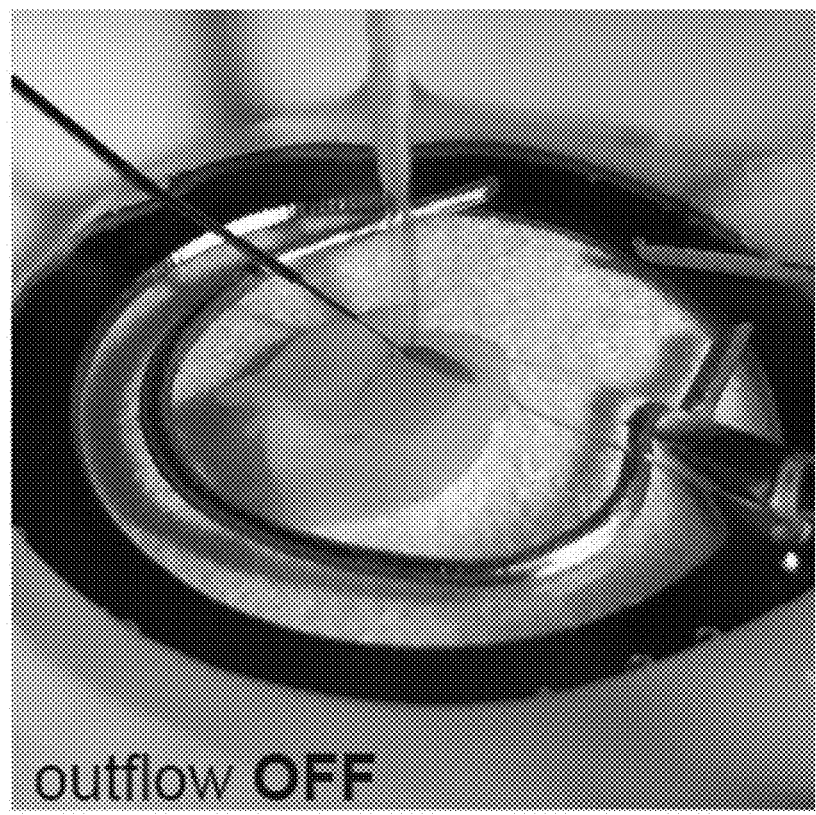
Figure 4C:
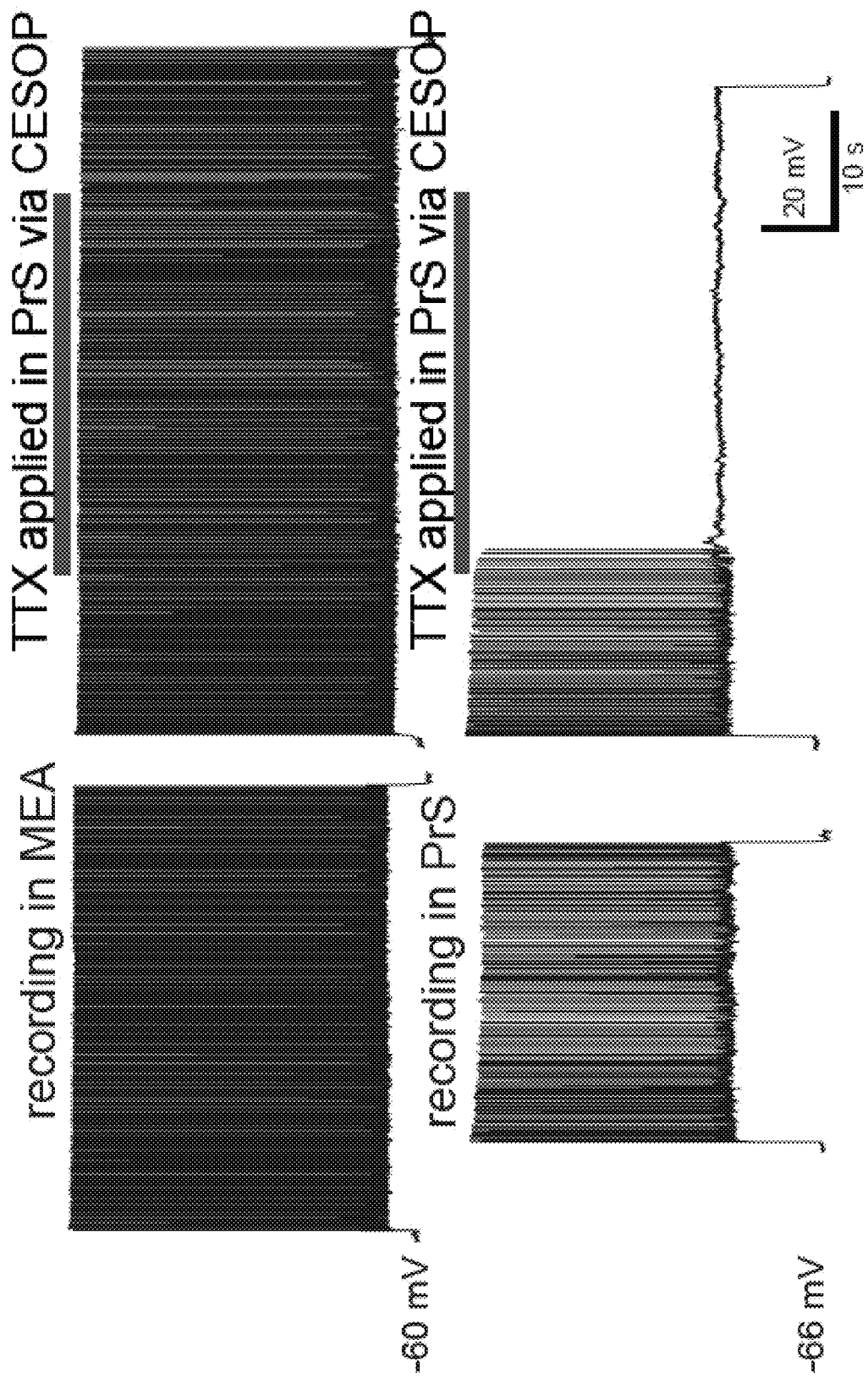
FIG. 4C depicts in the upper illustration differential effects of focal application of TTX (1 µM) in PrS on action potential discharge of a LIII pyramidal neuron in MEA, triggered by depolarizing current injections.
Figure 4D:
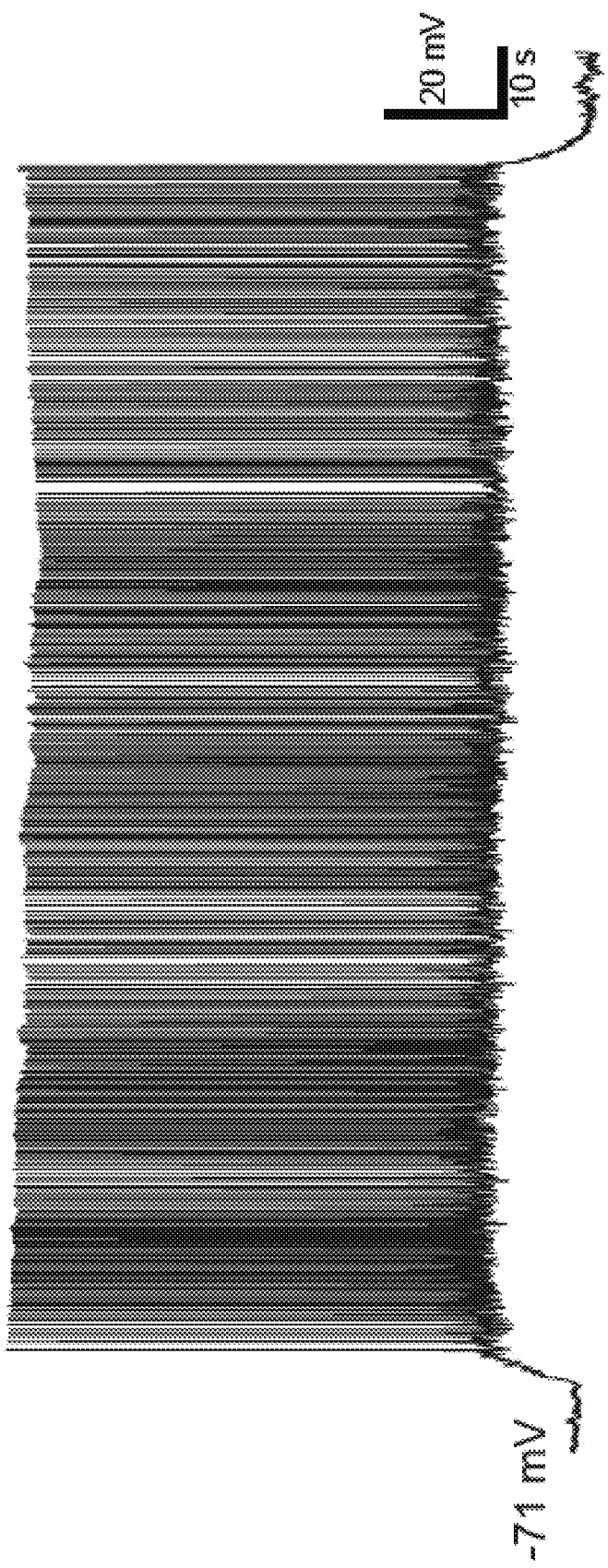
FIG. 4D depicts sustained action potential discharge triggered in a RS cell in LIII of PrS in response to local application of glutamate (100 µM; 3 min duration) via CESOP. Resting membrane potentials in recorded neurons are indicated juxtaposed to the respective traces.
Figure 4E:
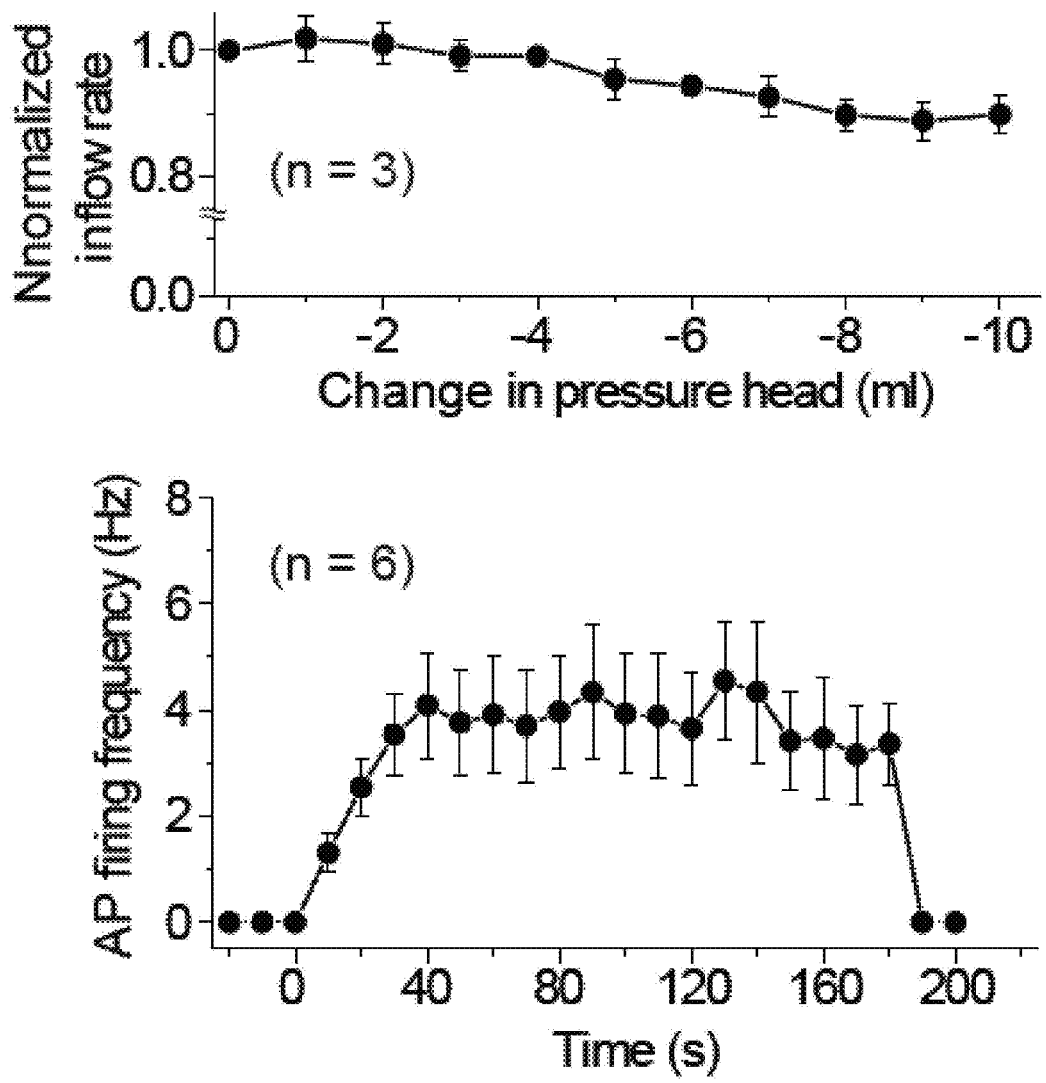
FIG. 4E shows that there is no significant change in the averaged normalized inflow rate as pressure head decreases in the range indicated (top panel), and focal application of glutamate via CESOP reliably evokes action potential firing in PrS neurons (bottom panel).

CESOP (FIGS. 4A & 4B) is a microfluidic technique used herein for focal application of pharmacological compounds that restricts their spillover to neighboring nuclei when studying interactions between juxtaposed brain structures such as the PrS and MEA (FIG. 4C). Glutamate (100 μM)/NBQX (10 μM) delivered via CESOP was used to enhance/suppress overall synaptic activity of PrS neurons (FIG. 4D). Slices were first treated with glutamate followed by NBQX and no more than one neuron per slice was used in assaying drug effects. PrS connectivity with recorded MEA neurons was confirmed using electrical stimulation of the PrS prior to use of CESOP. Note that recording intervals for EPSCs and IPSCs in MEA neurons correlated with periods of sustained action potential firing of PrS neurons depolarized by focal glutamate application via CESOP (FIGS. 4D & 4E bottom panel). Spontaneous (s-) EPSCs and sIPSCs were measured by holding the recorded neurons at −70 mV and 0 mV respectively, and recordings from control animals enabled baseline measurements of synaptic activity within these neuronal populations for comparison with epileptic animals. Differences in kinetic properties of postsynaptic currents between control and epileptic animals were assessed in aCSF by measuring rise times (RT; 10-90%) and decay time constants ($\tau$) of the averaged composite response of all events recorded under each condition.

C. PrS Contributes More to Synaptic Inhibition of LII Stellate Cells than Excitation Under Epileptic Conditions Contrary to expectations, focal application of glutamate to PrS in control tissue did not significantly alter average baseline sEPSC frequency (aCSF: 6±1 Hz; glutamate: 7.9±1.6 Hz, p>0.1, paired t-test) or amplitude (aCSF: 20±2 pA; glutamate 20±2 pA; p>0.9, paired t-test) in LII stellate cells, and subsequent application of NBQX also failed to elicit significant reductions in average sEPSC frequency (NBQX: 5.6±1 Hz) and amplitude (NBQX: 18±1 pA; FIGS. 5A, 5C, 5D, and 8). Overall, these data suggest that PrS contribution to the excitatory dive of LII stellate cell is minimal in control animals.

Figures 5A, 5B:
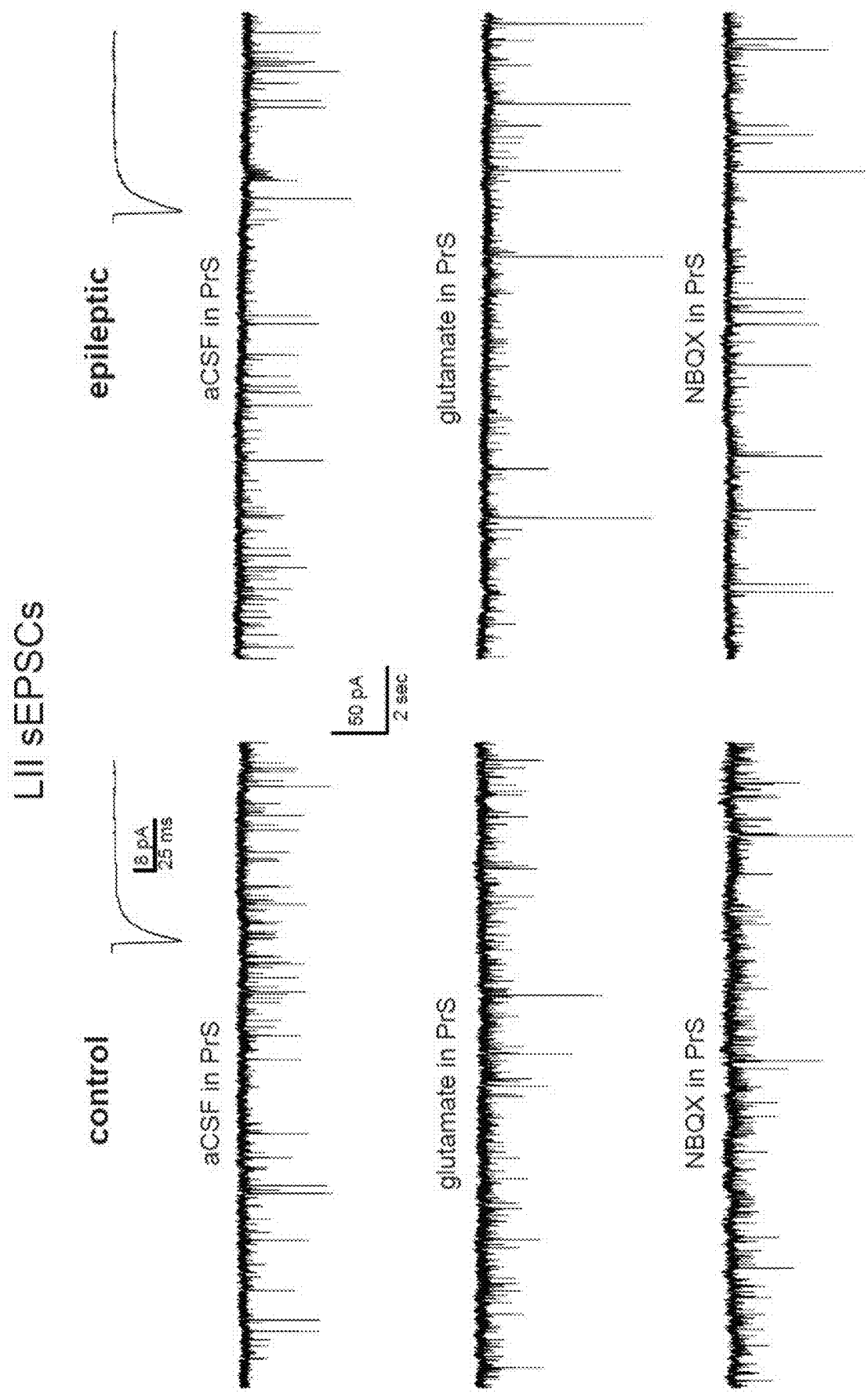
FIG. 5A depicts voltage-clamp recordings (20 s) of spontaneous excitatory postsynaptic currents (sEPSCs, inward events recorded at −70 mV holding potential) recorded in a LII stellate cell from control rats under the indicated conditions (aCSF, top; 100M glutamate, middle; 10 µM NBQX, bottom). Insets, averaged composite responses of all events recorded for the representative traces (in aCSF) under the indicated conditions.
FIG. 5B depicts voltage-clamp recordings (20 s) of spontaneous excitatory postsynaptic currents (sEPSCs, inward events recorded at −70 mV holding potential) recorded in a LII stellate cell from epileptic rats under the indicated conditions (aCSF, top; 100 µM glutamate, middle; 10 µM NBQX, bottom). Insets, averaged composite responses of all events recorded for the representative traces (in aCSF) under the indicated conditions.
Figure 5C:
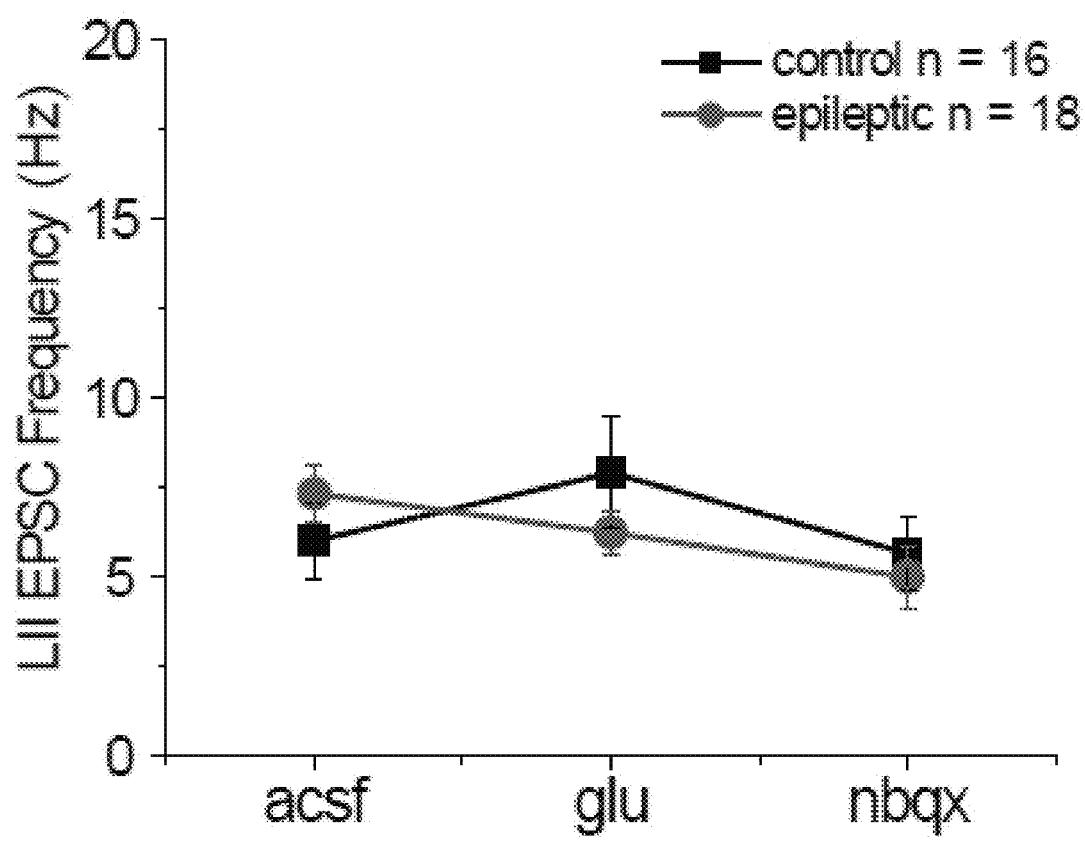
FIG. 5C shows plots of averaged frequency versus experimental condition for sEPSCs in 1 min-long recordings from LII stellate cells in control and epileptic rats under the indicated conditions.
Figure 5D:
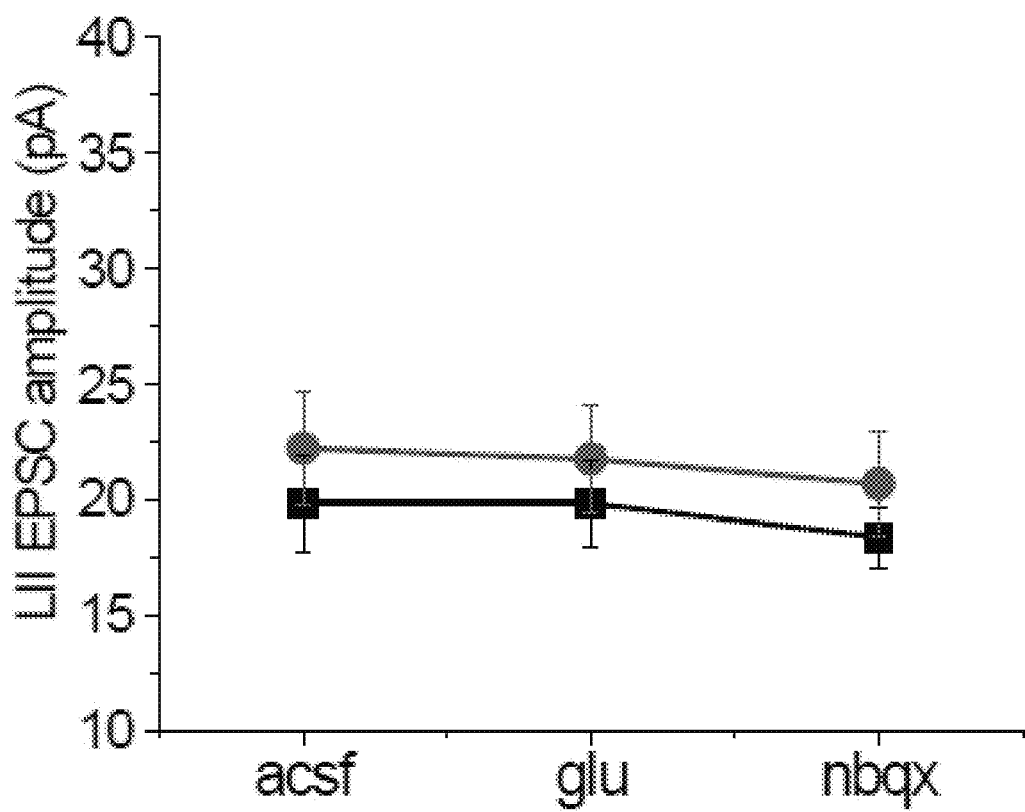
FIG. 5D shows plots of averaged sEPSC amplitudes corresponding to data presented in FIG. 5C. Collectively, FIGS. 5A-SD show that excitatory synaptic drive is comparable between control and epileptic rats and not greatly influenced by PrS input.

The baseline excitatory drive to LII stellate cells in epileptic rats (in aCSF) was comparable to controls, with averaged sEPSC frequency (epileptic: 7.3±0.8 Hz; control: 6±1 Hz; p>0.3, t-test) and amplitude (epileptic: 22±2 pA; control: 20±2 pA; p>0.4, t-test) being similar for both groups (FIGS. 5B-SD). As with control animals, focal application of glutamate or NBQX to PrS in epileptic animals failed to produce significant changes in average frequency (glutamate: 6.2±0.6 Hz; NBQX: 4.9±0.8 Hz; p>0.08, paired t-test) or amplitude (glutamate: 22±2 pA; NBQX: 21±2 pA; p>0.1, paired t-test) of sEPSCs (FIGS. 5B-5D). Kinetic properties of sEPSCs recorded in these neurons were similar between control ($\tau$: 7.5±0.4, RT: 1.6±0.1 ms) and epileptic ($\tau$: 6.8±0.2, RT: 1.3-0.05 ms) groups although RTs for EPSCs tended to be faster in epileptic tissue (p=0.1, 0.004 for $\tau$ and RT respectively, t-test; insets, FIGS. 5A & 5B). Together, these data suggest that baseline excitatory drive to LII stellate cells is comparable between control and epileptic rats, and that PrS contributes only minimally to altering the excitatory synaptic drive of LII stellate cells in both groups.

Figures 5E, 5F:
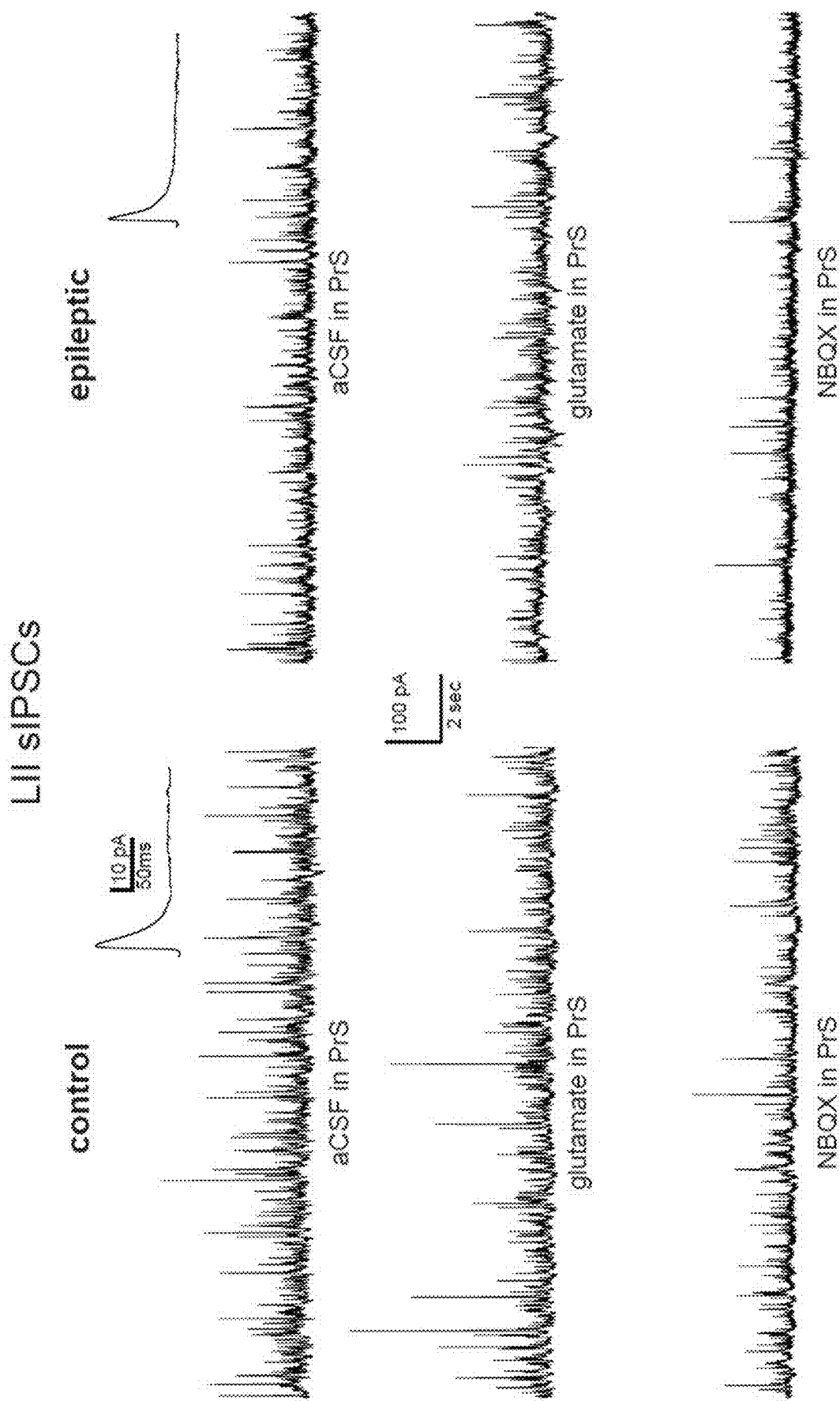
FIG. 5E depicts voltage-clamp recordings (20 s) of spontaneous inhibitory postsynaptic currents (sIPSCs, outward events recorded at 0 mV holding potential) recorded in a LII stellate cell from control rats under the indicated conditions (aCSF, top; 100 µM glutamate, middle; 10 µM NBQX, bottom). Insets, averaged composite responses of all events recorded for the representative traces (in aCSF) under the indicated conditions.
FIG. 5F depicts voltage-clamp recordings (20 s) of spontaneous inhibitory postsynaptic currents (sIPSCs, outward events recorded at 0 mV holding potential) recorded in a LII stellate cell from epileptic rats under the indicated conditions (aCSF, top; 100 µM glutamate, middle; 10 µM NBQX, bottom). Insets, averaged composite responses of all events recorded for the representative traces (in aCSF) under the indicated conditions.
Figure 5G:
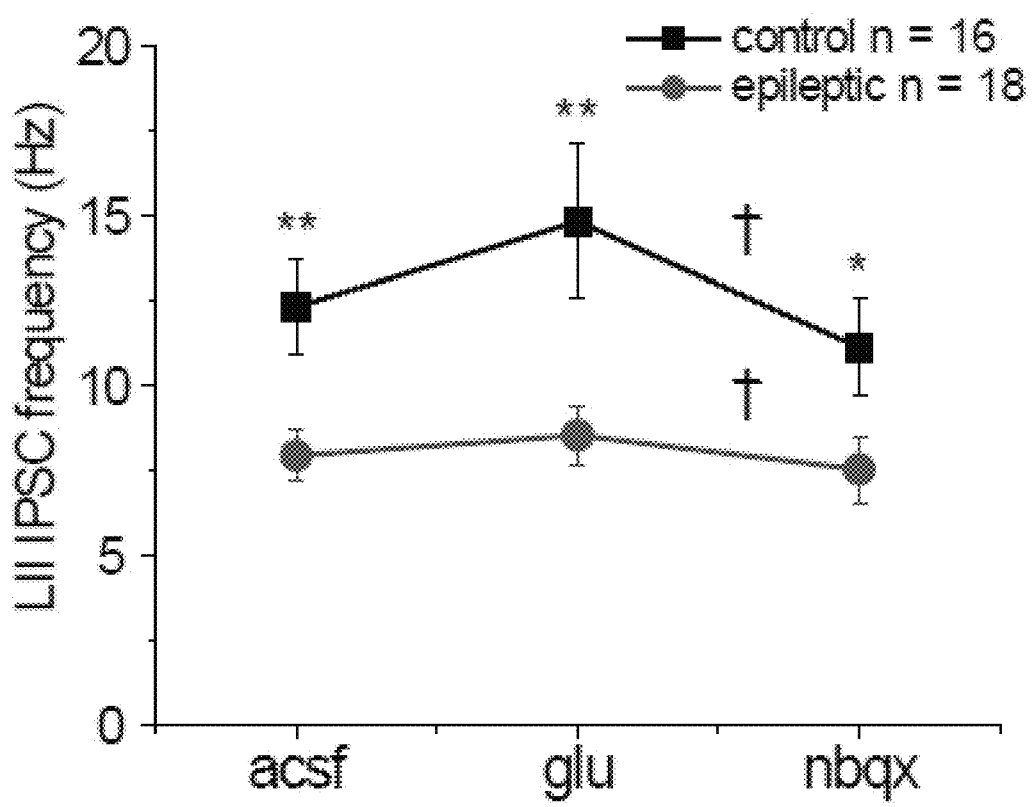
FIG. 5G shows plots of averaged frequency versus experimental condition for sIPSCs in 1 min-long recordings from LII stellate cells in control and epileptic rats under the indicated conditions.
Figure 5H:
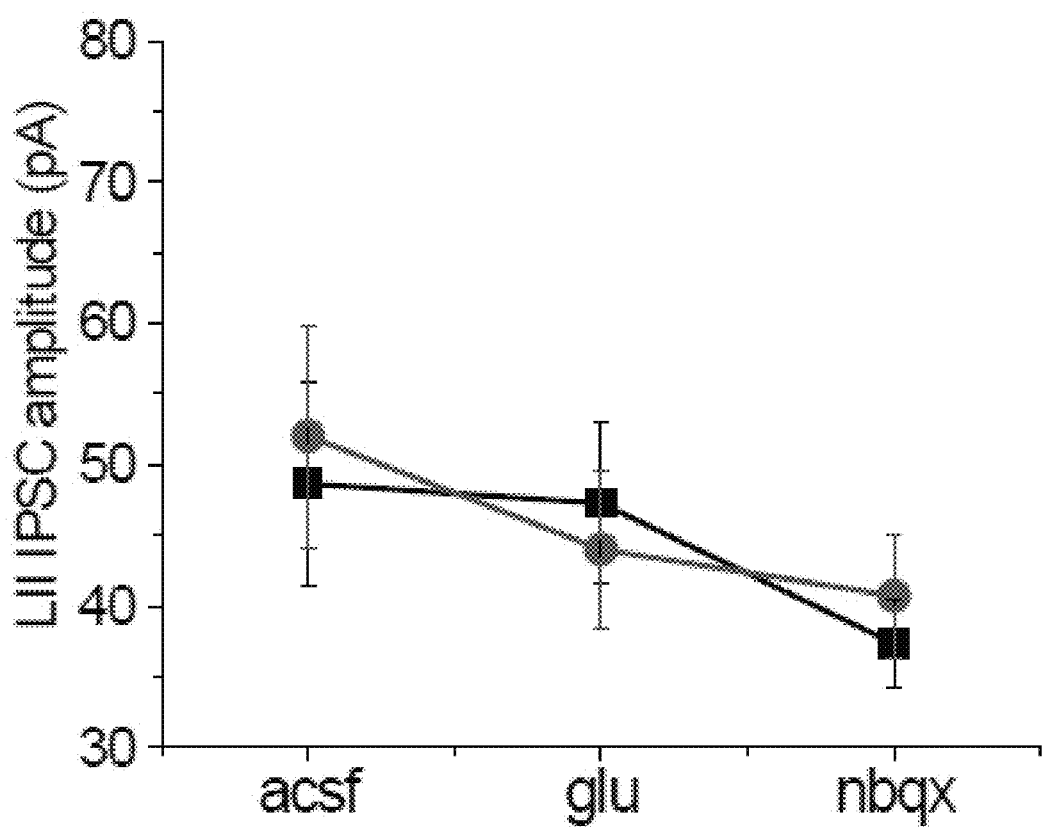
FIG. 5H shows plots of averaged sIPSC amplitudes corresponding to data presented in G. Error bars, where these are bigger than the size of the symbols used, represent SEM. †, $p<0.05$, paired t-test; *, $p<0.05$, , $p<0.01$, *, $p<0.001$, unpaired t-test. Collectively.

Synaptic inhibition in LII stellate cells is greatly reduced in epileptic rats (36% reduction) as suggested by a significantly lower averaged baseline sIPSC frequency (in aCSF; control: 12.3±1.4 Hz; epileptic: 7.9±0.7 Hz; p<0.01, t-test) while sIPSC amplitudes remained similar between both groups (control: 48±7 pA; epileptic: 52±8 pA; p=0.75, i-test; FIGS. 5E-5H & 8). While focal application of glutamate to PrS in control animals did not alter average sIPSC frequency significantly (glutamate: 14.8±2.3 Hz; p=0.14, paired t-test), application of NBQX, on the other hand, significantly reduced sIPSC frequency (NBQX: 11.1±1.4 Hz; p<0.05, paired t-test; FIG. 5G). Stellate cells from epileptic animals showed similar trends as controls, with NBQX alone producing a significant reduction in sIPSC frequency (glutamate: 8.5±0.9 Hz; NBQX: 7.5±1 Hz; p<0.05, paired t-test; FIGS. 5F & 5G). Suppression of inhibitory synaptic activity in PrS with NBQX was less efficacious in epileptic rats, given that there was a smaller percentage reduction in sIPSC frequency following application of the drug under epileptic conditions (11% reduction in epileptic versus 22% in control animals). Kinetic properties of sIPSCs recorded in these neurons were similar between control ($\tau$: 16.6±1.0, RT: 2.0±0.1 ms) and epileptic ($\tau$: 15.1±0.5, RT: 1.9±0.1 ms) groups (p=0.2, 0.5 for $\tau$ and RT respectively, t-test; insets, FIGS. 5E & 5F). Taken together, this data suggests that PrS likely has a greater influence on inhibitory synaptic activity of LII stellate cell than excitatory synaptic activity. Though conserved, this influence appears to be reduced in epileptic animals, congruent with an overall reduction in synaptic inhibition of these cells.

Figures 6A, 6B:
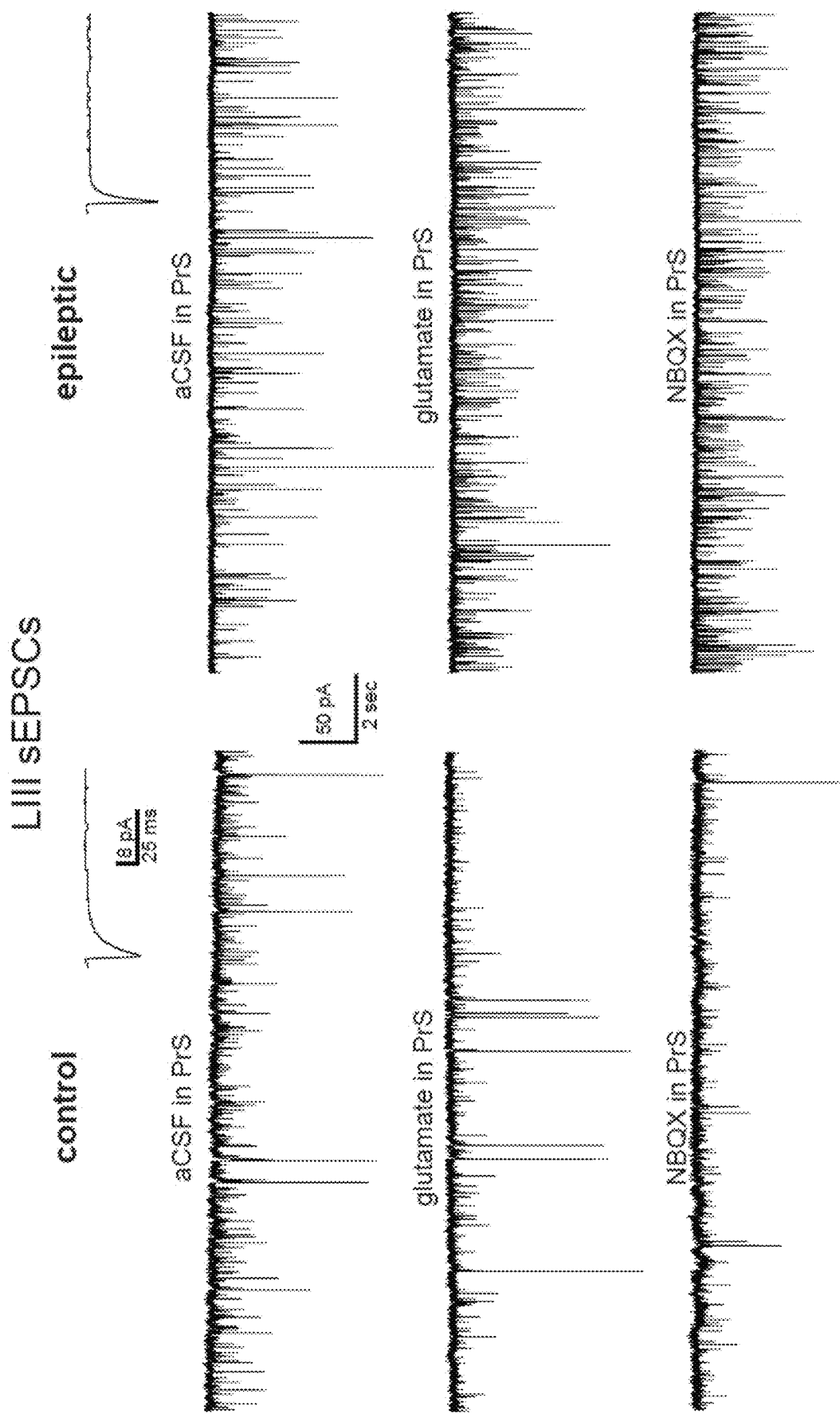
FIG. 6A depicts voltage-clamp recordings (20 s) of spontaneous excitatory postsynaptic currents (sEPSCs, inward events recorded at −70 mV holding potential) recorded in a LIII pyramidal cell from control rats under the indicated conditions (aCSF, top; 100 µM glutamate, middle; 10 µM NBQX, bottom). Insets, averaged composite responses of all events recorded for the representative traces (in aCSF) under the indicated conditions.
FIG. 6B depicts voltage-clamp recordings (20 s) of spontaneous excitatory postsynaptic currents (sEPSCs, inward events recorded at −70 mV holding potential) recorded in a LIII pyramidal cell from epileptic rats under the indicated conditions (aCSF, top; 100 µM glutamate, middle; 10 µM NBQX, bottom). Insets, averaged composite responses of all events recorded for the representative traces (in aCSF) under the indicated conditions.
Figure 6C:
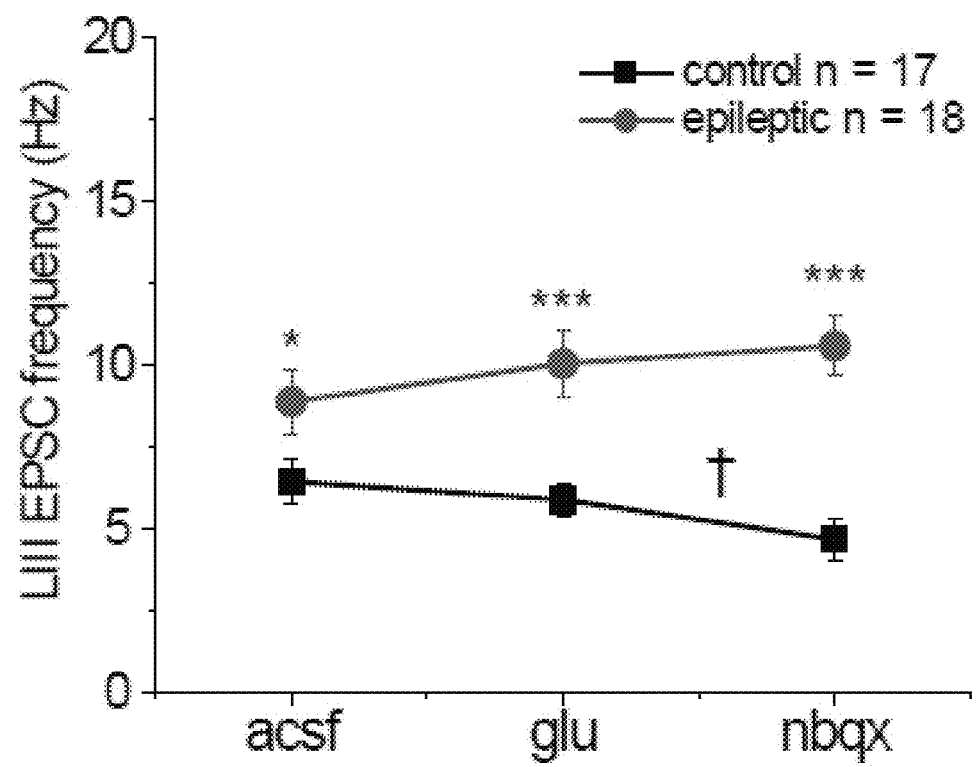
FIG. 6C shows plots of averaged frequency versus experimental condition for sEPSCs in 1 min-long recordings from LIII pyramidal cell in control and epileptic rats under the indicated conditions.
Figure 6D:
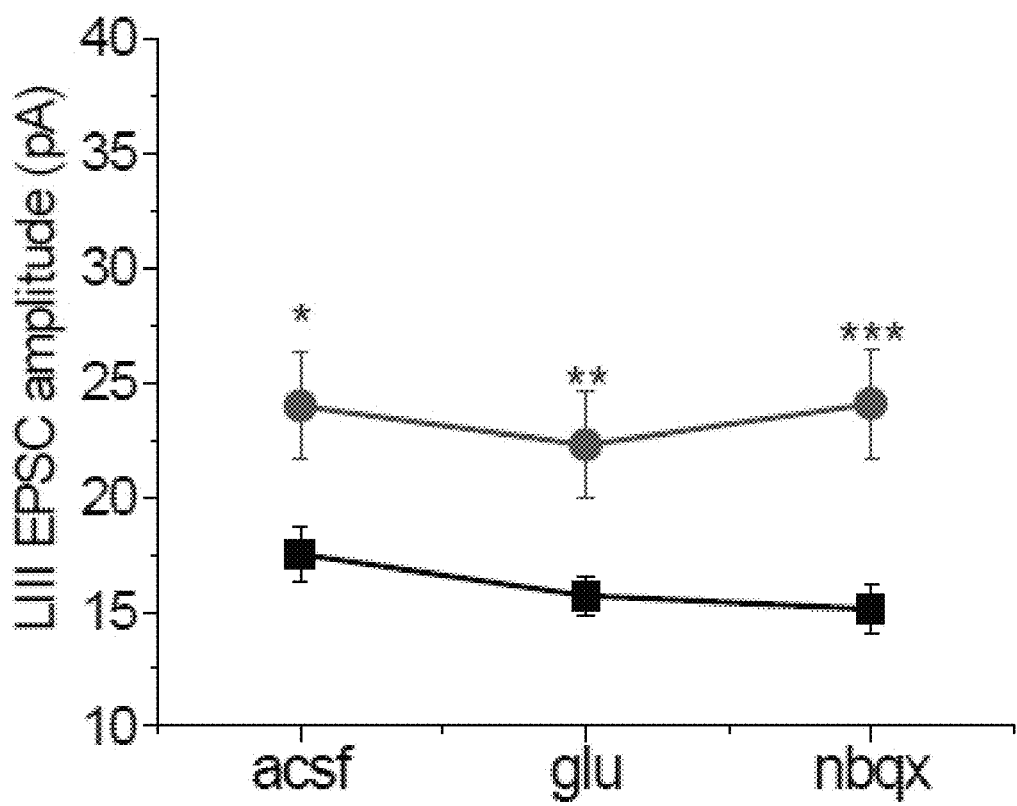
FIG. 6D shows plots of averaged sEPSC amplitudes corresponding to data presented in FIG. 6C. Collectively.

D. PrS-Mediated Synaptic Drive to LII Pyramidal Neurons in MEA is Altered in Epileptic Rats Focal application of glutamate to PrS in control animals did not significantly alter average baseline sEPSC frequency (aCSF: 6.4±0.7 Hz; glutamate: 5.9±0.5 Hz; p>0.3, paired t-test) in LIII pyramidal neurons, while suppressing synaptic activity with NBQX, on the other hand, resulted in a significant decrease in sEPSC frequency (NBQX: 4.6±0.6 Hz; p<0.05, paired 1-test; FIGS. 6A, 6C, and 8) suggesting that excitatory synaptic drive in these neurons is already maximal under baseline conditions. Averaged EPSC amplitudes were similar under all experimental conditions (p>0.1, paired t-test; FIGS. 6A, 6D, and 8). Compared with controls, averaged baseline sEPSC frequency (control: 6.4±0.7 Hz; epileptic: 8.9±1 Hz, 138% of control; p<0.05, t-test) and amplitude (control: 17±1 pA; epileptic: 24±2 pA, 141% of control, p<0.05, t-test) were significantly enhanced in the epileptic animals (FIGS. 6A, 6C, 6D, and 8). There was no significant shift in baseline sEPSC frequency or amplitude following application of glutamate in PrS in the epileptic animals (glutamate: 10±1 Hz, and 22±2 pA, respectively; p>0.1, paired t-test; FIGS. 6B-6D & 8). Surprisingly, application of NBQX to PrS failed to produce any significant reductions in sEPSC frequency under epileptic conditions (10.5±2 Hz; p>0.5, paired t-test; FIGS. 6B, 6C, and 8). The 30% reduction in sEPSC frequency noted following application of NBQX under control conditions was no longer observed under epileptic conditions. Kinetic properties of sEPSCs recorded in these neurons were faster in epileptic ($\tau$: 6.2±0.5, RT: 1.1±0.1 ms) compared to control ($\tau$: 9.1±0.4, RT: 1.5±0.1 ms) tissue (p<0.001 for both $\tau$ and RT, t-test; insets, FIGS. 6A & 6B).

Figures 6E, 6F:
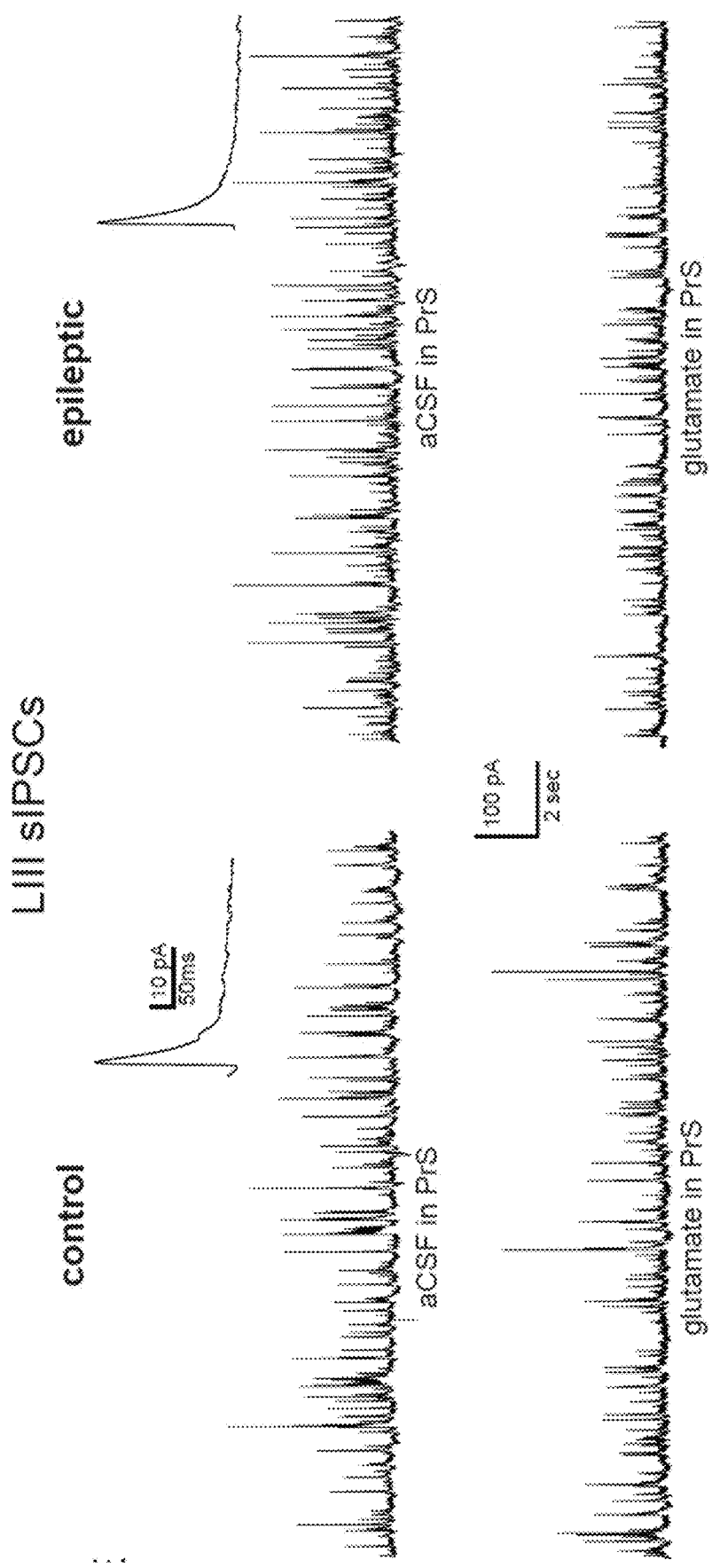
FIG. 6E depicts voltage-clamp recordings (20 s) of spontaneous inhibitory postsynaptic currents (sIPSCs, outward events recorded at 0 mV holding potential) recorded in a LIII pyramidal cell from control rats under the indicated conditions (aCSF, top; 100 µM glutamate, middle; 10 µM NBQX, bottom). Insets, averaged composite responses of all events recorded for the representative traces (in aCSF) under the indicated conditions.
FIG. 6F depicts voltage-clamp recordings (20 s) of spontaneous inhibitory postsynaptic currents (sIPSCs, outward events recorded at 0 mV holding potential) recorded in a LIII pyramidal cell from epileptic rats under the indicated conditions (aCSF, top; 100 µM glutamate, middle; 10 µM NBQX, bottom). Insets, averaged composite responses of all events recorded for the representative traces (in aCSF) under the indicated conditions.
Figure 6G:
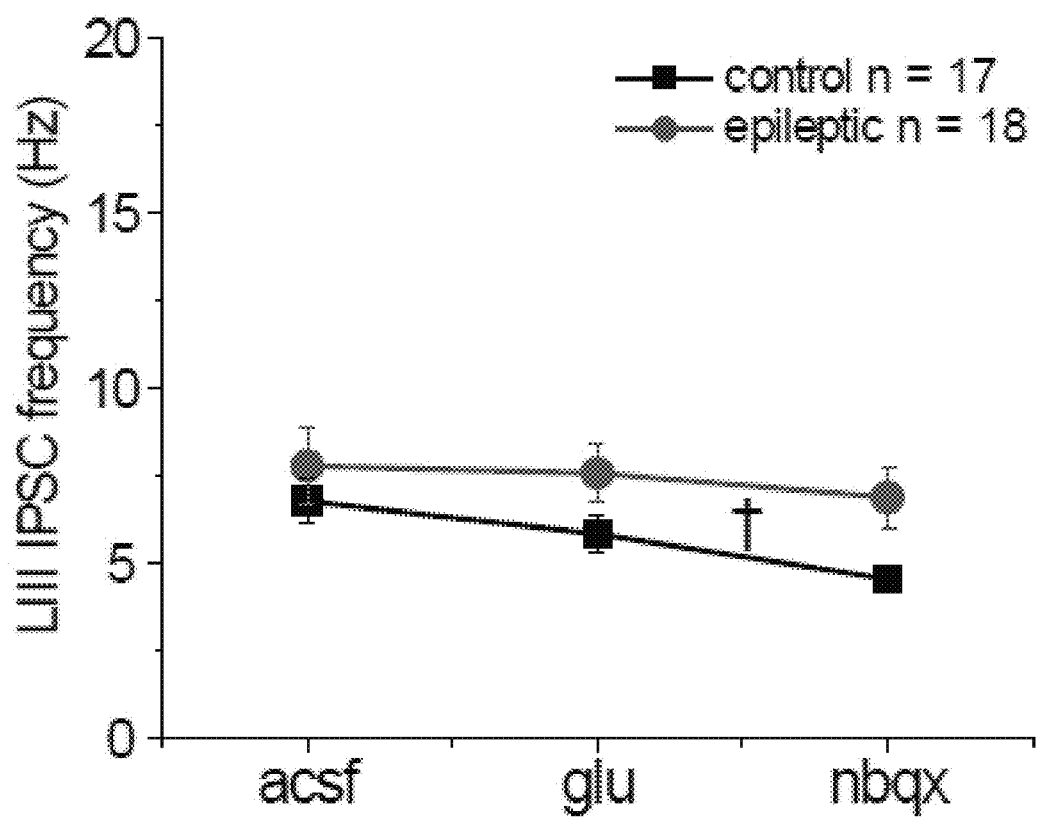
FIG. 6G shows plots of averaged frequency versus experimental condition for sIPSCs in 1 min-long recordings from LIII pyramidal cell in control and epileptic rats under the indicated conditions.
Figure 6H:
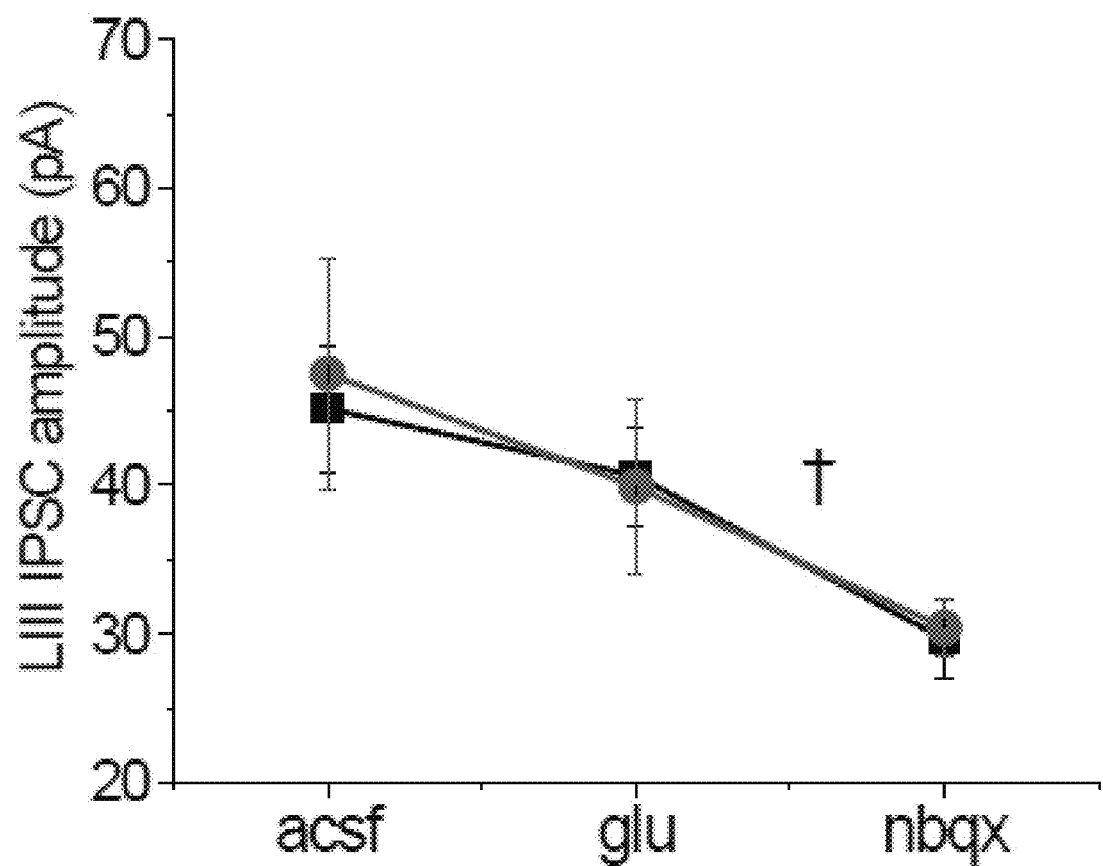
FIG. 6H shows plots of averaged sIPSC amplitudes corresponding to data presented in G. Error bars, where these are bigger than the size of the symbols used, represent SEM. †, $p<0.05$, paired t-test; *, $p<0.05$, , $p<0.01$, *, $p<0.001$, unpaired t-test. Collectively.

Averaged sIPSC frequency (control: 6.8±7 Hz; epileptic: 7.8±1 Hz; p>0.06, t-test) and amplitudes (control: 45±4 pA; epileptic: 47±8 pA; p>0.7, t-test) in LIII pyramidal cells from epileptic animals were similar to those in controls (FIGS. 6E-6H, and 8). However, sIPSCs in epileptic tissue ($\tau$: 12.8±0.9, RT: 1.9±0.2 ms) tended to be faster compared with control tissue ($\tau$: 17.7±0.7, RT: 2.0±0.1 ms; p=0.001, 0.4 for $\tau$ and RT respectively, t-test; insets, FIGS. 6E & 6F). Application of NBQX to PrS significantly reduced sIPSC frequency in control animals (glutamate: 5.8±0.5 Hz; NBQX: 4.5±0.3; p<0.05, paired 1-test; FIGS. 6E, 6G, and 8). Given that glutamate is ineffective in enhancing sIPSC frequency, this data suggests that under control conditions, PrS contribution to baseline synaptic inhibition of LIII pyramidal neurons in MEA is already maximal. Focal application of neither glutamate nor NBQX to PrS significantly altered average baseline sIPSC frequency (glutamate: 7.6±0.8 Hz; NBQX: 6.8±0.9; p>0.3, paired t-test) or amplitude (glutamate: 40±6 pA; NBQX: 30±2; p>0.06, paired t-test) under epileptic conditions (FIGS. 6F-6H & 8). This fact combined with absence of a detectable PrS influence on sEPSC frequency suggests that PrS mediated synaptic drive to LIII pyramidal neurons in MEA is altered in epileptic rats.

III. Discussion

This study used the CESOP technique/device, discussed herein, to focally apply a drug without spillover, thus enabling assessments of TLE-related changes in PrS input to principal neurons in superficial layers of MEA through comparison of synaptic properties under control and chronically epileptic conditions. It was found that monosynaptic input from PrS to MEA neurons is conserved in epileptic rats. Despite layer-specific changes in synaptic properties—large amplitude population discharges were recorded in both LII and LIII following PrS stimulation. Further, PrS contributes more to synaptic inhibition of LII stellate cells than excitation—baseline synaptic inhibition of LII stellate cells is significantly reduced in epileptic rats. Additionally, PrS contributes to both synaptic excitation and inhibition of LIII pyramidal cells under control conditions. However, alterations in PrS-mediated synaptic drive to LIII pyramidal neurons are masked despite an overall increase in excitatory synaptic drive to these neurons under epileptic conditions. These layer-specific alterations in PrS-MEA functional-connectivity are unexpected and of importance in piecing together the pathophysiological mechanism underlying TLE.

A. Properties of PrS-Mediated Synaptic Input to MEA Neurons

Electrical stimulation of PrS was used to confirm that PrS inputs to recorded neurons in the MEA were preserved and to determine whether synaptic properties, including activation thresholds and levels of facilitation, in LII stellate cells and LIII pyramidal neurons in epileptic rats were similar to control animals. PrS evoked responses displayed paired-pulse facilitation when ISIs were brief, and paired-pulse depression when ISIs were increased, suggesting that PrS excitatory input to MEA neurons is mediated by low probability of release synapses with a relatively slow (>500 ms) recovery time for the readily releasable pool of vesicles. In epileptic rats, changes in synaptic properties were mainly restricted to LII, where stellate cells had a larger paired-pulse facilitation over a broader range of ISIs compared to cells from control animals. Alterations in release probability potentially influence spontaneous synaptic activity, but baseline sEPSC frequency for LII stellate cells in epileptic rats was similar to controls. Besides altered release probability, changes in calcium buffering and signal integration properties may also contribute to increased paired-pulse facilitation in LII stellate cells under epileptic conditions.

The large amplitude epileptogenic events observed in LII and LIII neurons following PrS stimulation exclusively in epileptic rats likely reflect network hyperexcitability and hypersynchrony within the MEA, similar to PrS triggered aberrant MEA activity described previously. MEA hyperexcitability could also be attributable to the activation of excitatory afferents from sources other than PrS, or stem from alterations in local circuitry, including reduced network inhibition following loss of vulnerable GABAergic interneurons and/or local network reorganization supporting hyperactivation of superficial layers of MEA.

B. Changes in PrS-Mediated Synaptic Drive to MEA Neurons

Mechanisms underlying hyperexcitability of neurons in superficial MEA seem to be layer-specific, while LII stellate cells are rendered hyperexcitable because of reduced inhibition LIII pyramidal neurons are rendered hyperexcitable on account of enhanced excitation. The apparent distinction in how alterations in synaptic drive mediate hyperexcitability of these neurons complements the observation that under normal conditions, inhibitory synaptic drive in LII stellate cells is significantly greater than in LIII pyramidal neurons, as confirmed in the recordings of baseline synaptic drive to these neurons in control animals. Previous studies have proposed synaptic reorganization of PrS afferents contacting surviving neurons in LIII and neighboring LII following loss of LIII neurons as a potential mechanism for MEA hyperexcitability (Scharfman et al. 1998; Tolner et al. 2005). This data does not support synaptic restructuring of afferents between PrS and LII under epileptic conditions and suggests a minimal contribution of PrS, if at all, to LII stellate cell hyperexcitability. However, compromised inhibitory synaptic drive might underlie LII pathophysiology. This data suggests that PrS contributes significantly to synaptic inhibition of LII stellate cells in the MEA. This contribution could either be directly through GABAergic projecting neurons, and/or via afferents to local interneurons within MEA that mediate feed-forward inhibition of neurons in layers II and III. The reduced inhibitory synaptic drive noted in LII stellate cells under epileptic conditions is consistent with diminution of PrS-mediated synaptic inhibition arising in part from either loss of GABAergic neurons in PrS, including MEA-targeting projection neurons, loss of local GABAergic interneurons in MEA, and/or down-regulation of GABA subunits mediating tonic inhibition. The loss of GABAergic neurons in PrS is substantiated by the absence of stuttering cells in epileptic rats (Abbasi S. and Kumar SS. Electrophysiological and morphological characterization of cells in superficial layers of rat presubiculum. *The Journal of comparative neurology* 521: 3116-3132, 2013; Abbasi S, and Kumar SS. Regular-spiking cells in the presubiculum are hyperexcitable in a rat model of temporal lobe epilepsy. *Journal of neurophysiology* 112: 2888-2900, 2014).

Enhanced excitatory synaptic drive in LIII pyramidal neurons under epileptic conditions may arise from the formation of new synapses between target-deprived afferents from PrS and surviving LIII neurons (Scharfman et al. 1998; Tolner et al. 2005). These data with focal application of glutamate in the PrS, however, did not indicate an increased PrS influence of surviving LIII pyramidal neurons in MEA. These results suggest that PrS-mediated excitatory input to LIII pyramidal neurons is already maximal under baseline conditions as focal application of glutamate to PrS failed to significantly shift baseline sEPSC frequency. Furthermore, the fact that excitatory synaptic drive to these neurons is unaltered following application of NBQX to PrS, albeit elevated under epileptic conditions, suggests an increased excitability of inputs from sources other than PrS, including neurons in deep layers of MEA, CAI and/or the subiculum. Anatomical studies have posited that projections from deep layer neurons within MEA provide direct excitatory input to and support feed-forward inhibition of superficial layer neurons, and are of importance to MEA function. Furthermore, it is known that these deep layer neurons receive input directly from PrS and the parasubiculum, and together may be of significance in propagating aberrant activity to superficial layers under conditions of enhanced excitability. A possible explanation for why a reduction in frequency of postsynaptic currents in LIII pyramidal neurons was not seen following focal application of NBQX to PrS relates to the previous observation that excitatory drive to RS cells, the predominant cell type in PrS, is significantly reduced under epileptic conditions and is comprised mostly of non-action potential dependent events (Abbasi S. and Kumar SS. Regular-spiking cells in the presubiculum are hyperexcitable in a rat model of temporal lobe epilepsy. Journal of neurophysiology 112: 2888-2900, 2014).

Figure 7:
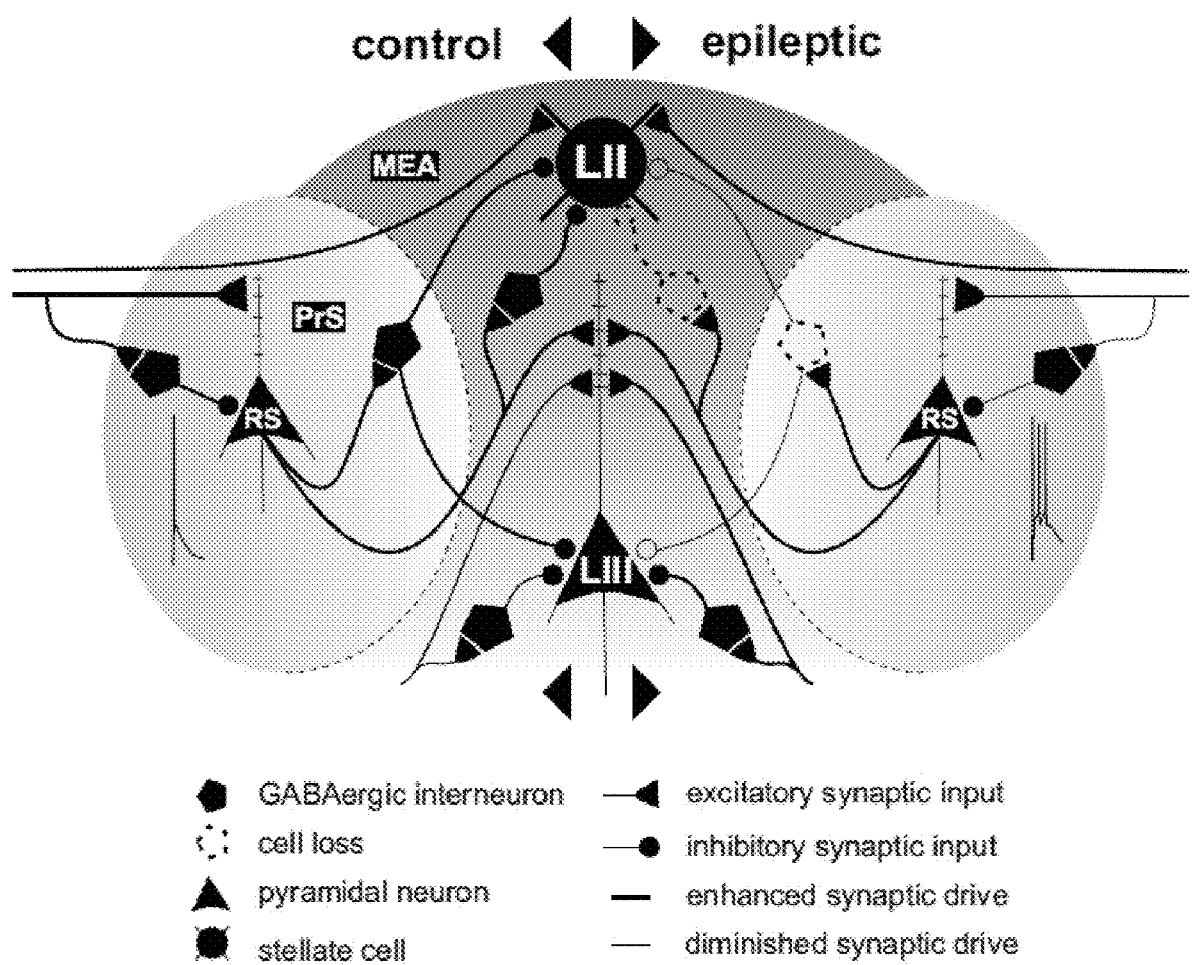
FIG. 7 is a schematic of functional circuitry underlying possible changes in excitatory and inhibitory synaptic drive to LII stellate cells and LIII pyramidal neurons in the MEA under control and epileptic conditions deduced from this study. The PrS provides both glutamatergic and GABAergic projections to superficial layers of the MEA, and RS cells, the predominant cell type in the PrS, have been shown to become hyperexcitable in TLE.

In conclusion, the forgoing results and analysis enable synthesis of a conceptual model for PrS-MEA interactions under control and epileptic conditions (FIG. 7), using the CESOP method/device to show the effect of drug application to the PrS on the MEA. Layer II stellate cells are hyperexcitable in TLE on account of GABAergic inhibition from PrS and locally within MEA being compromised. Hyperexcitability of LIII pyramidal cells ensues more from disruption of the balance between excitation and inhibition, with PrS contributing equally to both under control conditions. RS cells, the predominant cell type in the PrS are hyperexcitable in TLE due in part to reduced excitation and feed-forward inhibition (Abbasi S, and Kumar SS. Regular-spiking cells in the presubiculum are hyperexcitable in a rat model of temporal lobe epilepsy. *Journal of neurophysiology* 112: 2888-2900, 2014). Neither glutamate nor NBQX applied focally within PrS influences LII stellate cell excitability under control/epileptic conditions because PrS contributes minimally to excitatory synaptic dive of these neurons. Because NBQX application significantly reduces inhibitory synaptic drive, while glutamate application remains ineffective, PrS contribution to LII stellate cell inhibition is maximal under baseline control conditions.

Under epileptic conditions, it could be seen (using the CESOP device/methodology) that glutamate does not alter inhibitory synaptic drive to stellate cells, while NBQX still reduces synaptic inhibition, though this effect is now smaller on account of loss of GABAergic neurons within PrS and locally within MEA. Glutamate does not affect excitatory/ inhibitory synaptic drive to LIII pyramidal neurons, while NBQX reduces both under control conditions, suggesting that PrS contributes to both excitation and inhibition of these neurons maximally under baseline conditions. Under epileptic conditions, PrS effect on LIII neuronal excitability is masked by enhanced activity of neurons targeting LIII pyramids from sources other than the PrS. Together these data highlight layer-specific modulation of MEA excitability by PrS, and enable formulation of a functional circuit that underlies PrS-MEA interactions. These interactions and this relationship between PrS and MEA could only be seen by using the CESOP technique/device, as the PrS and MEA are juxtaposed or otherwise in close proximity to each other. Using conventional devices and methodologies, there would be a spillover effect of both glutamate and NBQX from PrS to MEA, thus compromising what the relationship between the two regions actually is. Understanding this relationship now, however, provides treatment options for TLE, in particular, though it can be seen how the current invention can be broadly applied to drug discovery and actual treatments of various diseases and disorders.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Glossary of Claim Terms

Concomitant election and suction of a perfusate: This term is used herein to refer to an objective of the current invention, specifically being to simultaneously discharge and suction perfusate to and from a region of interest. This allows the perfusate to effectuate a reaction within the region of interest or a neighboring region, while also preventing spillover into the neighboring region.

Control mechanism: This term is used herein to refer to any structural component that is capable of regulating the flow of perfusate through the lines/manifolds.

Distal: This term is used herein to refer to positioning further from a user/operator of the CESOP device and closer to the ROI.

Inflow manifold: This term is used herein to refer to a line or tubing through which perfusate flows from a cistern to an anatomical region of interest at a controlled rate.

Juxtaposed anatomical region: This term is used herein to refer to an anatomical area that is adjacent to or otherwise in close proximity to the region of interest where the perfusate is delivered. The proximity of the two regions is such that there would be risk of spillover of the perfusate from the region where the perfusate is delivered to this neighboring region.

Nearly simultaneously: This term is used herein to refer to two events occurring virtually concurrently. This term "nearly" is used to indicate that the perfusate typically needs a miniscule amount of time in the region of interest to effectuate a reaction within that region or within a neighboring region. This time may be nanoseconds, milliseconds, etc., depending on the perfusate, the region of interest, the reaction to be observed, etc.

Outflow manifold: This term is used herein to refer to a line or tubing through which perfusate suctions/flows out of an anatomical region of interest at a controlled rate.

Proximal: This term is used herein to refer to positioning closer to a user/operator of the CESOP device and further from the ROI.

Rate of suction: This term is used herein to refer to the degree to which perfusate is removed from the region of interest through the outflow line.

Reaction: This term is used herein to refer to a response in a region of interest or a neighboring region based on delivery of a perfusate (e.g., drug) to that region of interest.

Region of interest: This term is used herein to refer to an anatomical area where a perfusate (e.g., drug) is to be delivered to effectuate a reaction within that area or within a neighboring area.

Rigid support member: This term is used herein to refer to any structural component capable of maintaining the connection between the inflow and outflow lines, such that regardless of where the inflow line is positioned to deliver perfusate, the outflow line is present adjacent thereto to suction out that perfusate.

Staggered: This term is used herein to refer to the distal ends of the inflow and outflow tips being offset or otherwise not terminating at exactly the same longitudinal point.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An assembly for identifying a region of interest and for concomitant ejection and suction of a perfusate within a region of interest without spillover of said perfusate to a juxtaposed anatomical region, comprising:
   a recording chamber containing artificial cerebrospinal fluid, such that a tissue slice is submergible in the fluid and disposed within the recording chamber, the tissue slice having a region of interest and a juxtaposed anatomic region;
   an electrode disposed within the recording chamber, the electrode adapted to be disposed on the tissue slice to identify a region of interest as indicated by responses from neurons within the tissue slice; and
   a concomitant ejection and suction device in communication with the recording chamber and adapted to interact with the region of interest identified by the electrode, the concomitant ejection and suction device including:
   an inflow manifold having a proximal end and a distal end, said proximal end of said inflow manifold being coupled to a cistern containing said perfusate to be delivered to said region of interest;
   an outflow manifold having a proximal end and a distal end, said proximal end of said outflow manifold being coupled to a reservoir and an outflow control mechanism to control a rate of suction of said perfusate out of said region of interest and into said reservoir,
   wherein said inflow manifold and said outflow manifold are directly or indirectly coupled to each other;
   an inflow tip disposed at said distal end of said inflow manifold;
   an outflow tip disposed at said distal end of said outflow manifold, said inflow tip and said outflow tip externally juxtaposed from and in a staggered relationship with to each other and collectively forming a microfluidic application tip of said device,
   such that said microfluidic application tip both discharges and suctions said perfusate into and out of said region of interest nearly simultaneously while allowing said perfusate to effectuate a reaction within said region of interest or said juxtaposed anatomical region, the reaction being measured by the electrode, and wherein as said inflow manifold discharges said perfusate into said region of interest, said outflow manifold nearly simultaneously suctions said perfusate out of said region of interest so that said perfusate cannot spillover into said juxtaposed anatomical region from said region of interest.

2. A device as in claim 1, further comprising an inflow control mechanism coupled to said inflow manifold.

3. A device as in claim 2, wherein said inflow control mechanism includes a stopper or a regulator.

4. A device as in claim 1, wherein said perfusate flows through said inflow manifold under gravity-fed negative pressure.

5. A device as in claim 1, wherein said outflow control mechanism is a variable speed peristaltic pump.

6. A device as in claim 1, wherein said outflow control mechanism includes a stopper or a regulator.

7. A device as in claim 1, wherein said outflow tip has an inner diameter larger than an inner diameter of said inflow tip to ensure that said outflow manifold suctions said perfusate out of said region of interest.

8. A device as in claim 7, wherein said inner diameter of said outflow tip is about 750 μm and said inner diameter of said inflow tip is about 250 μm.

9. A device as in claim 1, wherein said inflow tip and said outflow tip are staggered at their distal tips.

10. A device as in claim 1, wherein said inflow manifold and said outflow manifold are indirectly coupled to each other via a rigid support member to permit precise positioning of said microfluidic application tip.

11. A device as in claim 10, wherein said rigid support member is an elongate rod disposed between said inflow manifold and said outflow manifold.

12. A device as in claim 1, further comprising a micromanipulator to position said microfluidic application tip precisely within said region of interest.

13. A device as in claim 1, wherein said cistern is a multi-barrel gravity fed perfusion system coupling multiple drug reservoirs.

14. A device as in claim 1, wherein a flow rate of said perfusate through said outflow manifold is higher than a flow rate of said perfusate through said inflow manifold.

15. An assembly for identifying a region of interest and for concomitant ejection and suction of a perfusate within a region of interest without spillover of said perfusate to a juxtaposed anatomical region, comprising:
   a recording chamber containing artificial cerebrospinal fluid, such that a tissue slice is submergible in the fluid and disposed within the recording chamber, the tissue slice having a region of interest and a juxtaposed anatomic region;

an electrode disposed within the recording chamber, the electrode adapted to be disposed on the tissue slice to identify a region of interest as indicated by responses from neurons within the tissue slice; and a concomitant ejection and suction device in communication with the recording chamber and adapted to interact with the region of interest identified by the electrode, the concomitant ejection and suction device including an inflow manifold having a proximal end and a distal end, said proximal end of said inflow manifold being coupled to a cistern containing said perfusate to be delivered to said region of interest;

an inflow control mechanism coupled to said inflow manifold, wherein said inflow control mechanism includes a stopper or a regulator;

an outflow manifold having a proximal end and a distal end, said proximal end of said outflow manifold being coupled to a reservoir and an outflow control mechanism to control a rate of suction of said perfusate out of said region of interest and into said reservoir, wherein said outflow control mechanism includes a variable speed peristaltic pump and a stopper or a regulator;

an inflow tip disposed at said distal end of said inflow manifold;

an outflow tip disposed at said distal end of said outflow manifold, wherein said outflow tip has an inner diameter larger than an inner diameter of said inflow tip to ensure that said outflow manifold suctions said perfusate out of said region of interest, said inflow tip and said outflow tip externally juxtaposed from and in a staggered relationship with each other and collectively forming a microfluidic application tip of said device, such that said microfluidic application tip both discharges and suctions said perfusate into and out of said region of interest nearly simultaneously while allowing said perfusate to have a measurable effect within said region of interest, wherein as said inflow manifold discharges said perfusate into said region of interest, said outflow manifold nearly simultaneously suctions said perfusate out of said region of interest so that said perfusate cannot spillover into said juxtaposed anatomical region from said region of interest; and a micromanipulator to position said microfluidic application tip precisely within said region of interest;

wherein said inflow manifold and said outflow manifold are indirectly coupled to each other via a rigid support member to permit precise positioning of said microfluidic application tip, said rigid support member being an elongate rod disposed between said inflow manifold and said outflow manifold, wherein a flow rate of said perfusate through said outflow manifold is higher than a flow rate of said perfusate through said inflow manifold.

* * * * *